US012508054B2

(12) United States Patent
Åberg et al.

(10) Patent No.: US 12,508,054 B2
(45) Date of Patent: Dec. 30, 2025

(54) IMPLANTS FOR FILLING BORE HOLES IN BONE AND METHODS FOR FILLING BORE HOLES IN BONE

(71) Applicant: OSSDSIGN AB, Uppsala (SE)

(72) Inventors: Jonas Åberg, Uppsala (SE); Ghanim Ibrahim, Uppsala (SE); Thomas Engstrand, Uppsala (SE)

(73) Assignee: OSSDSIGN AB, Uppsala (SE)

( * ) Notice: Subject to any disclaimer, the term of this patent is extended or adjusted under 35 U.S.C. 154(b) by 1184 days.

(21) Appl. No.: 17/286,218

(22) PCT Filed: Oct. 15, 2019

(86) PCT No.: PCT/IB2019/058796
§ 371 (c)(1),
(2) Date: Apr. 16, 2021

(87) PCT Pub. No.: WO2020/079597
PCT Pub. Date: Apr. 23, 2020

(65) Prior Publication Data

US 2021/0338286 A1 Nov. 4, 2021

Related U.S. Application Data

(60) Provisional application No. 62/746,305, filed on Oct. 16, 2018.

(51) Int. Cl.
*A61B 17/68* (2006.01)
*A61F 2/28* (2006.01)

(52) U.S. Cl.
CPC .......... *A61B 17/688* (2013.01); *A61B 17/686* (2013.01); *A61F 2/2875* (2013.01); *A61F 2310/00353* (2013.01)

(58) Field of Classification Search
CPC .... A61B 17/686; A61B 17/688; A61B 2/2875
See application file for complete search history.

(56) References Cited

U.S. PATENT DOCUMENTS 4,905,679 A 3/1990 Morgan
5,152,836 A 10/1992 Hirano et al.
(Continued)

FOREIGN PATENT DOCUMENTS

CN 1688263 A 10/2005
CN 101360461 A 2/2009
(Continued)

OTHER PUBLICATIONS

Hirayama et al, Properties of Calcium Phosphate Cements With Different Tetracalcium Phosphate and Dicalcium Phosphate Anhydrous Molar Ratios, Journal of Research of the National Institute of Standards and Technology, vol. 113, pp. 311-320 (2008).
(Continued)

*Primary Examiner* — Erin Mcgrath
(74) *Attorney, Agent, or Firm* — Porter Wright Morris & Arthur LLP

(57) ABSTRACT

An implant for at least partially filling a bore hole in a bone includes a biocompatible plate and a support structure. The support structure has a ring-shaped inner support frame having an outer surface defining the outer diameter of the inner support frame and an inner surface, and an outer support frame having a plurality of fastening points adapted for attaching the implant to bone surrounding a bore hole in which the plate is inserted. The outer support frame is connected to and extends away from the outer surface of the inner support frame. A method of forming the implant is also provided.

16 Claims, 17 Drawing Sheets

(56) References Cited

U.S. PATENT DOCUMENTS

| | | | |
|---|---|---|---|
| 5,201,737 | A | 4/1993 | Leibinger et al. |
| 5,338,356 | A | 8/1994 | Hirano et al. |
| 5,368,602 | A | 11/1994 | De la Torre |
| 5,468,242 | A | 11/1995 | Reisberg |
| 5,503,164 | A | 4/1996 | Friedman |
| 5,578,036 | A * | 11/1996 | Stone ................. A61B 17/8085 606/281 |
| 5,605,713 | A | 2/1997 | Boltong |
| 5,683,667 | A | 11/1997 | Fulmer et al. |
| 5,690,631 | A | 11/1997 | Duncan et al. |
| 5,752,958 | A | 5/1998 | Wellisz |
| 5,766,176 | A | 6/1998 | Duncan |
| 5,782,971 | A | 7/1998 | Constantz et al. |
| 5,783,217 | A | 7/1998 | Lee et al. |
| 5,980,540 | A | 11/1999 | Bruce |
| 5,984,925 | A | 11/1999 | Apgar |
| 6,093,188 | A | 7/2000 | Murray |
| 6,117,456 | A | 9/2000 | Lee et al. |
| 6,206,957 | B1 | 3/2001 | Wenz et al. |
| 6,338,810 | B1 | 1/2002 | Carpena |
| 6,521,246 | B2 | 2/2003 | Sapieszko et al. |
| 6,642,285 | B1 | 11/2003 | Bohner et al. |
| 6,733,582 | B1 | 5/2004 | Bohner et al. |
| 6,863,899 | B2 | 3/2005 | Koblish et al. |
| 6,905,516 | B1 | 6/2005 | Lemaitre et al. |
| 6,991,803 | B2 | 1/2006 | Sapieszko et al. |
| 7,118,705 | B2 | 10/2006 | Lin |
| 7,175,858 | B2 | 2/2007 | Constantz et al. |
| 7,252,841 | B2 | 8/2007 | Constantz et al. |
| 7,318,841 | B2 | 1/2008 | Tofighi et al. |
| 7,351,280 | B2 | 4/2008 | Khairoun et al. |
| 7,407,542 | B2 | 8/2008 | Lemaitre et al. |
| 7,473,312 | B2 | 1/2009 | Barralet et al. |
| 7,501,018 | B2 | 3/2009 | Engqvist et al. |
| 7,655,047 | B2 | 2/2010 | Swords |
| 7,754,246 | B2 | 7/2010 | Mosley et al. |
| 7,833,253 | B2 | 11/2010 | Ralph et al. |
| 8,231,624 | B1 | 7/2012 | Strippgen |
| 8,246,663 | B2 | 8/2012 | Lovald et al. |
| 8,281,638 | B2 | 10/2012 | Metzger |
| 8,298,292 | B2 | 10/2012 | Swords et al. |
| 8,361,126 | B2 | 1/2013 | Perrow et al. |
| 8,366,751 | B2 | 2/2013 | Pfefferle |
| 2003/0082232 | A1 | 5/2003 | Lee et al. |
| 2003/0199615 | A1 | 10/2003 | Chaput et al. |
| 2004/0038180 | A1 | 2/2004 | Mayer et al. |
| 2005/0149032 | A1 | 7/2005 | Vaughen et al. |
| 2005/0216008 | A1 | 9/2005 | Zwirnmann et al. |
| 2006/0058802 | A1 | 3/2006 | Kofoed |
| 2006/0116682 | A1 | 6/2006 | Longo |
| 2006/0239884 | A1 | 10/2006 | Chane-Ching et al. |
| 2006/0263443 | A1 | 11/2006 | Chow et al. |
| 2007/0092856 | A1 | 4/2007 | Chow et al. |
| 2007/0173844 | A1 | 7/2007 | Ralph et al. |
| 2007/0189951 | A1 | 8/2007 | Constantz et al. |
| 2008/0027455 | A1 | 1/2008 | Bondeville |
| 2008/0028992 | A1 | 2/2008 | Lee et al. |
| 2008/0187571 | A1 | 8/2008 | Clineff et al. |
| 2008/0206300 | A1 | 8/2008 | Bohner et al. |
| 2009/0022771 | A1 | 1/2009 | Lynn et al. |
| 2009/0076617 | A1 | 3/2009 | Ralph et al. |
| 2009/0220475 | A1 | 9/2009 | Bohner et al. |
| 2010/0069455 | A1 | 3/2010 | Takato et al. |
| 2010/0095870 | A1 | 4/2010 | Insley et al. |
| 2010/0269736 | A1 | 10/2010 | Chow et al. |
| 2010/0303888 | A1 | 12/2010 | Barralet et al. |
| 2011/0014244 | A1 | 1/2011 | Sapieszko et al. |
| 2011/0054540 | A1 | 3/2011 | Ralph et al. |
| 2011/0152195 | A1 | 6/2011 | O'Mahony et al. |
| 2011/0158963 | A1 | 6/2011 | Font Perez et al. |
| 2012/0058152 | A1 | 3/2012 | Garcia de Castro Andrews et al. |
| 2013/0053900 | A1 | 2/2013 | Qwarnstrom et al. |
| 2013/0138114 | A1 | 5/2013 | Lin et al. |
| 2013/0310948 | A1 | 11/2013 | Luscher |
| 2016/0166358 | A1 | 6/2016 | Thome et al. |
| 2017/0239054 | A1 | 8/2017 | Engstrand et al. |
| 2018/0256361 | A1 | 9/2018 | Bishop et al. |

FOREIGN PATENT DOCUMENTS

| | | | |
|---|---|---|---|
| CN | 101528158 | A | 9/2009 |
| CN | 102008346 | A | 4/2011 |
| CN | 103221075 | A | 7/2013 |
| CN | 103857351 | A | 6/2014 |
| CN | 106361468 | A | 2/2017 |
| CN | 106999214 | A | 8/2017 |
| EP | 543765 | A1 | 5/1993 |
| EP | 544384 | B1 | 1/1996 |
| EP | 433852 | B1 | 3/1996 |
| EP | 1023032 | B1 | 1/2002 |
| EP | 910993 | B1 | 7/2002 |
| EP | 984745 | B1 | 10/2003 |
| EP | 936929 | B1 | 6/2004 |
| EP | 1380313 | B1 | 5/2005 |
| EP | 1178847 | B1 | 1/2007 |
| EP | 1420725 | B1 | 8/2008 |
| EP | 2014258 | A1 | 1/2009 |
| EP | 2030596 | A1 | 3/2009 |
| EP | 1298103 | B1 | 5/2011 |
| EP | 2474286 | A1 | 7/2012 |
| EP | 2529702 | A1 | 12/2012 |
| IN | 1919357 | A | 2/2007 |
| JP | 1-100049 | A | 4/1989 |
| JP | 2006-218050 | A | 8/2006 |
| JP | 2007-501054 | A | 1/2007 |
| JP | 5862726 | B1 | 2/2016 |
| WO | 95/20368 | A1 | 8/1995 |
| WO | 02/11781 | A1 | 2/2002 |
| WO | 02/22045 | A1 | 3/2002 |
| WO | 03/007831 | A1 | 1/2003 |
| WO | 2004/093734 | A2 | 11/2004 |
| WO | 2004/108019 | A2 | 12/2004 |
| WO | 2004/112859 | A1 | 12/2004 |
| WO | 2005/016616 | A1 | 2/2005 |
| WO | 2005/074453 | A2 | 8/2005 |
| WO | 2005/077049 | A2 | 8/2005 |
| WO | 2005/122956 | A2 | 12/2005 |
| WO | 2007/047921 | A2 | 4/2007 |
| WO | 2008/002595 | A2 | 1/2008 |
| WO | 2009/077210 | A1 | 6/2009 |
| WO | 2010/055483 | A2 | 5/2010 |
| WO | 2010/092001 | A1 | 8/2010 |
| WO | 2011/009635 | A1 | 1/2011 |
| WO | 2011/068451 | A2 | 6/2011 |
| WO | 2011/112145 | A1 | 9/2011 |
| WO | 2012/016200 | A1 | 2/2012 |
| WO | 2012/103164 | A1 | 8/2012 |
| WO | 2012/118843 | A1 | 9/2012 |
| WO | 2012/147114 | A1 | 11/2012 |
| WO | 2013/027175 | A2 | 2/2013 |
| WO | 2014/125381 | A2 | 8/2014 |
| WO | 2016/024248 | A1 | 2/2016 |

OTHER PUBLICATIONS

Desai et al, A Self-Setting, Monetite (CaHPO4) Cement for Skeletal Repair, Advances in Bioceramics and Biocomposites II, vol. 27, No. 6, pp. 61-69 (Nov. 2006).

Bohner et al, Technological issues for the development of more efficient calcium phosphate bone cements: A critical assessment, Biomaterials, vol. 26, pp. 6423-6429 (2005).

Xu, Hockin H. K. et al, Premixed macroporous calcium phosphate cement scaffold, Journal of Materials Science, Materials in Medicine, vol. 18, pp. 1345-1353 (2007).

Barralet et al, Ionic midification of calcium phosphate cement viscosity. Part II: hypodermic injection and strength improvement of brushite cement, Biomaterials, vol. 25, pp. 2197-2203 (2004).

Habraken et al, Ceramic composites as matrices and scaffolds for drug delivery in tissue engineering, Advance Drug Delivery Reviews, vol. 59, 234-248 (2007).

(56) References Cited

OTHER PUBLICATIONS

Han et al, B-TCP/MCPM-based premixed calcium phosphate cements, Acta Biomaterialia, vol. 5, pp. 3165-3177 (2009).
Office Action and Search Report dated Nov. 28, 2023 from corresponding Chinese Application No. 2019800692592, with English Translation.

* cited by examiner

FIG. 35
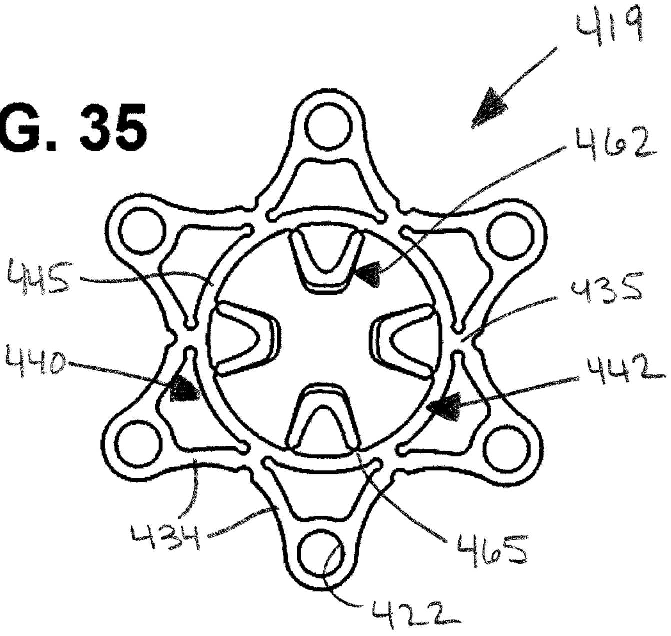
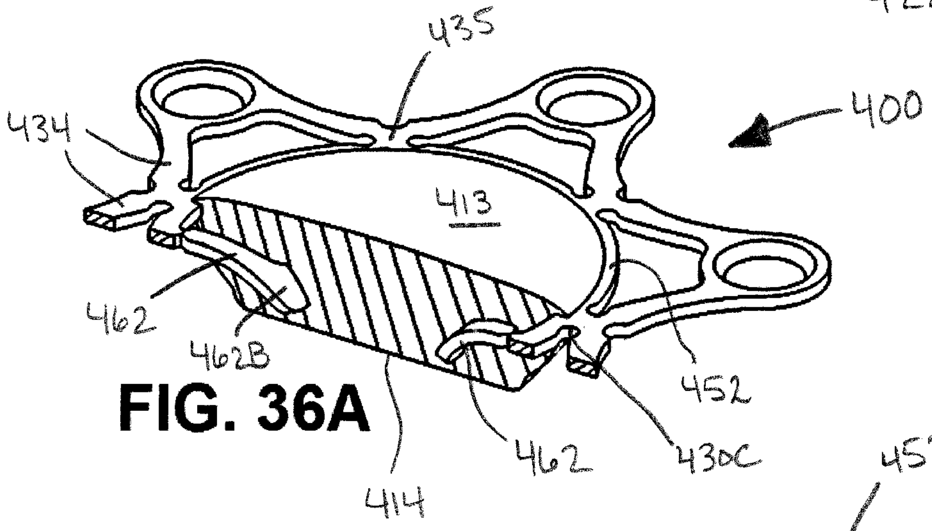
FIG. 36A
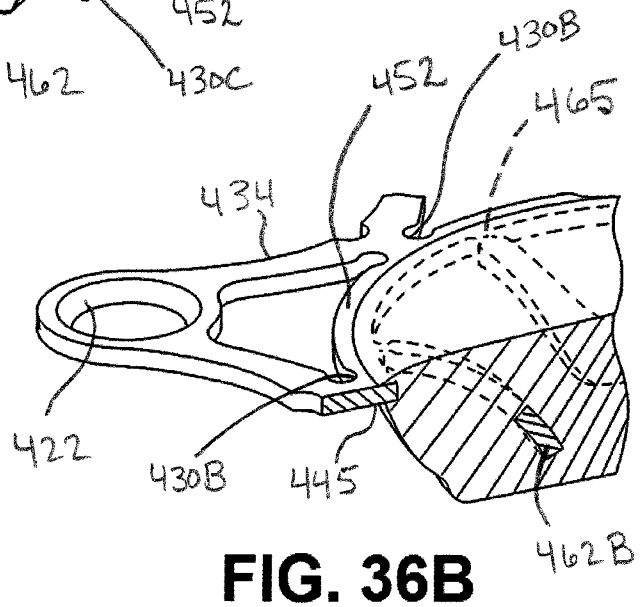
FIG. 36B

FIG. 37
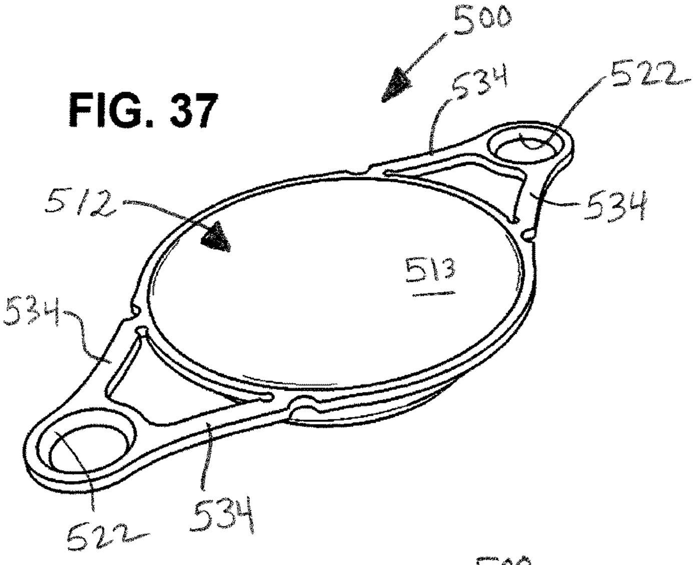
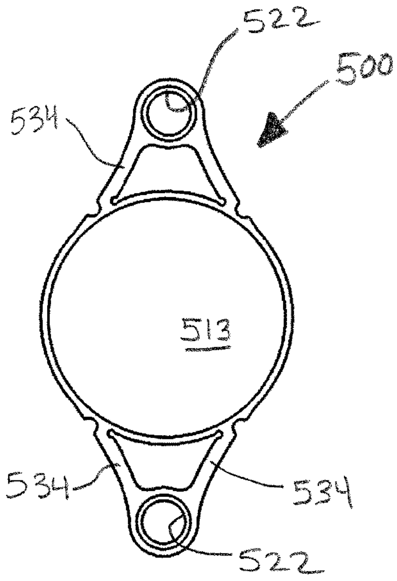
FIG. 38
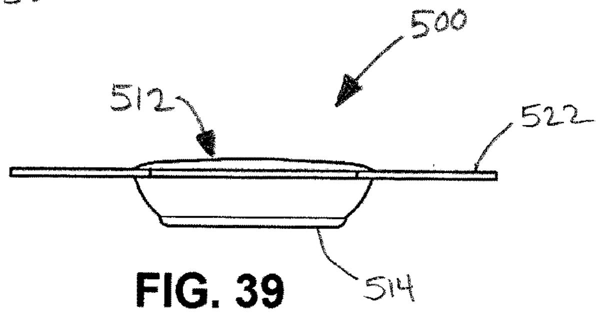
FIG. 39
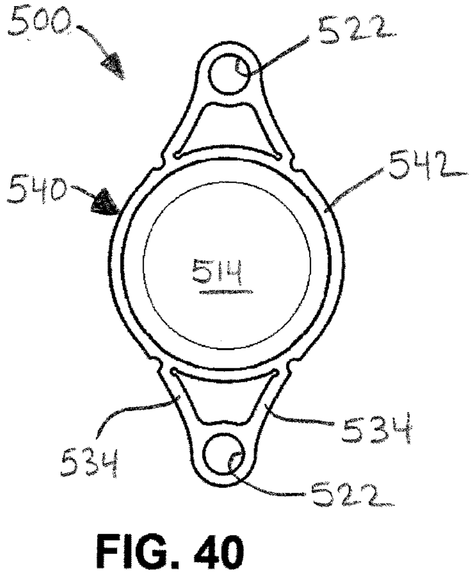
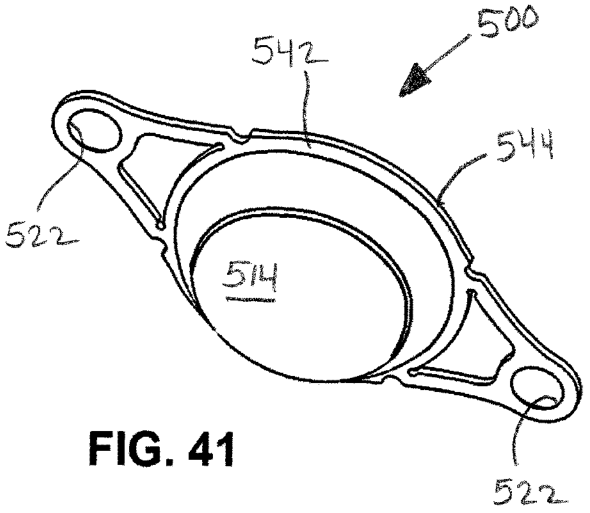
FIG. 41
FIG. 40

IMPLANTS FOR FILLING BORE HOLES IN BONE AND METHODS FOR FILLING BORE HOLES IN BONE

BACKGROUND

Surgical access beneath a patient's skull is necessary for a variety of reasons. Typically, one or more bore holes (also referred to as burr holes) are formed in the skull using a cranial perforator (essentially, a drill). In a craniotomy, for example, multiple bore holes are made in order to facilitate the removal of a bone flap for temporary access to the brain. The bone flap is formed by first drilling two or more (e.g., three) spaced-apart bore holes in the skull. The bore holes are then joined by saw cuts that, together with the bore holes, form a continuous cut line through the skull, thereby releasing a bone flap. The bone flap can be lifted to allow access to the underlying tissue. At the end of the procedure, the bone flap is (usually) replaced and reattached to the surrounding skull. Reattachment is done using sutures, metal wires, metal plates, metal mesh or other means. However, the bore holes seldom heal on their own, thereby compromising the protection normally provided by a fully intact skull. For this reason, when the bone flap is replaced, it is desirable not only to anchor it into place but also to at least partially fill the bore holes.

Similarly, one or more bore holes may also be made in a patient's skull in order to, for example, allow for the insertion of drainage tubes for draining a subdural hematoma. When the drainage tubes are removed, it is once again desirable to fill the bore hole(s) at least partially.

Bore holes are sometimes filled using autograph, allograph or synthetic scaffold materials in order to promote healing. Scaffold strategies often involve utilizing metal meshes or porous ceramic materials. Current strategies using metal mesh, however, do not induce tissue healing. Ceramics are typically utilized only to provide osteoconductive support but will not provide fixation of the bone flap to adjacent cranial bone. Most commonly, the bore holes are left untreated.

As an alternative, bore hole implants comprising a combination of a metal supporting frame and a biocompatible cement plate are described in Applicant's. U.S. Pub. No. 2013/0053900A1 ("the '900 App."), published on Feb. 28, 2013, entitled "Implants and Methods for Using Such Implants to Fill Holes in Bone Tissue;" PCT Pub. No. WO 2013/027175 ("the '175 App."), also published on Feb. 28, 2013, entitled "Implants and Methods for Using Such Implants to Fill Holes in Bone Tissue;" PCT Pub. No. WO 2014/125381 ("the '381 App."), published on Aug. 21, 2014, entitled "Mosaic Implants, Kits and Methods for Correcting Bone Defects;" and PCT Pub. No. WO 2016/024248 ("the '248 App."), published on Feb. 18, 2016, entitled "Bone Implants for Correcting Bone Defects." The foregoing patent publications are incorporated by reference herein.

While a variety of devices and techniques may exist for providing implants for filling holes in bone, it is believed that no one prior to the inventors has made or used an invention as described herein.

BRIEF DESCRIPTION OF THE DRAWINGS

While the specification concludes with claims that particularly point out and distinctly claim the invention, it is believed the present invention will be better understood from the following description of certain examples taken in conjunction with the accompanying drawings. In the drawings, like numerals represent like elements throughout the several views.

FIG. 23 depicts a top plan view of the support structure of the implant of FIG. 17.

FIG. 35 depicts a bottom plan view of the support structure of FIG. 32.

FIGS. 36A and 36B are cross-sectional views of the implant of FIG. 27.

FIG. 37 depicts a perspective view of a another embodiment of a bore hole implant.

FIGS. 38-41 depict a top plan view, side view, bottom plan view, and bottom perspective view, respectively, of the implant of FIG. 37.

Figure 1:
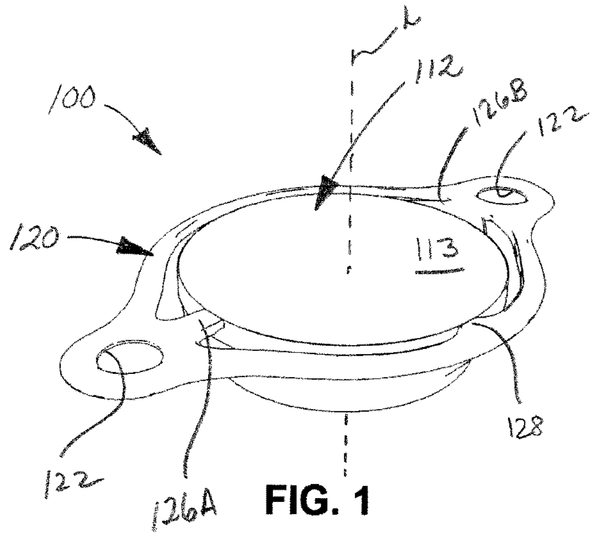
FIG. 1 depicts a perspective view of an embodiment of a bore hole implant suitable for use, for example, as a bore hole implant in a skull.
Figure 2:
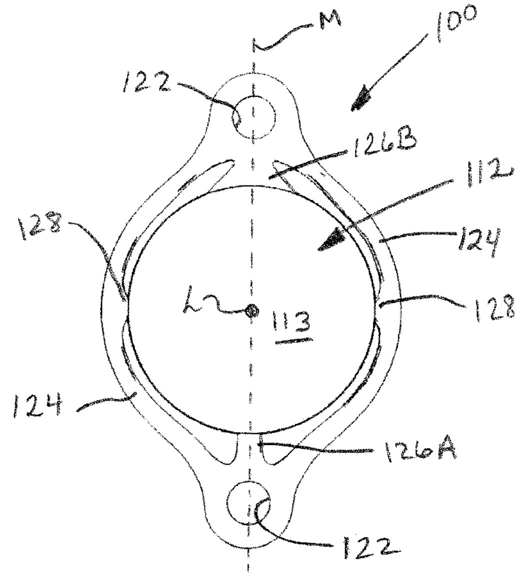
FIGS. 2-5 depict a top plan view, side view, bottom plan view, and bottom perspective view, respectively, of the implant of FIG. 1.

The drawings illustrate several aspects of the present invention, and together with the description serve to explain the principles of the invention. However, the invention is not limited to the precise arrangements shown, and it is contemplated that various embodiments of the invention may be carried out in a variety of other ways, including ways not necessarily depicted in the drawings.

DETAILED DESCRIPTION

The following description of certain examples should not be used to limit the scope of the present invention. Other features, aspects, and advantages of the versions disclosed herein will become apparent to those skilled in the art from the following description. As will be realized, the versions described herein are capable of other different and obvious aspects, all without departing from the invention. Accordingly, the drawings and descriptions should be regarded as illustrative in nature and not restrictive.

Figure 47:
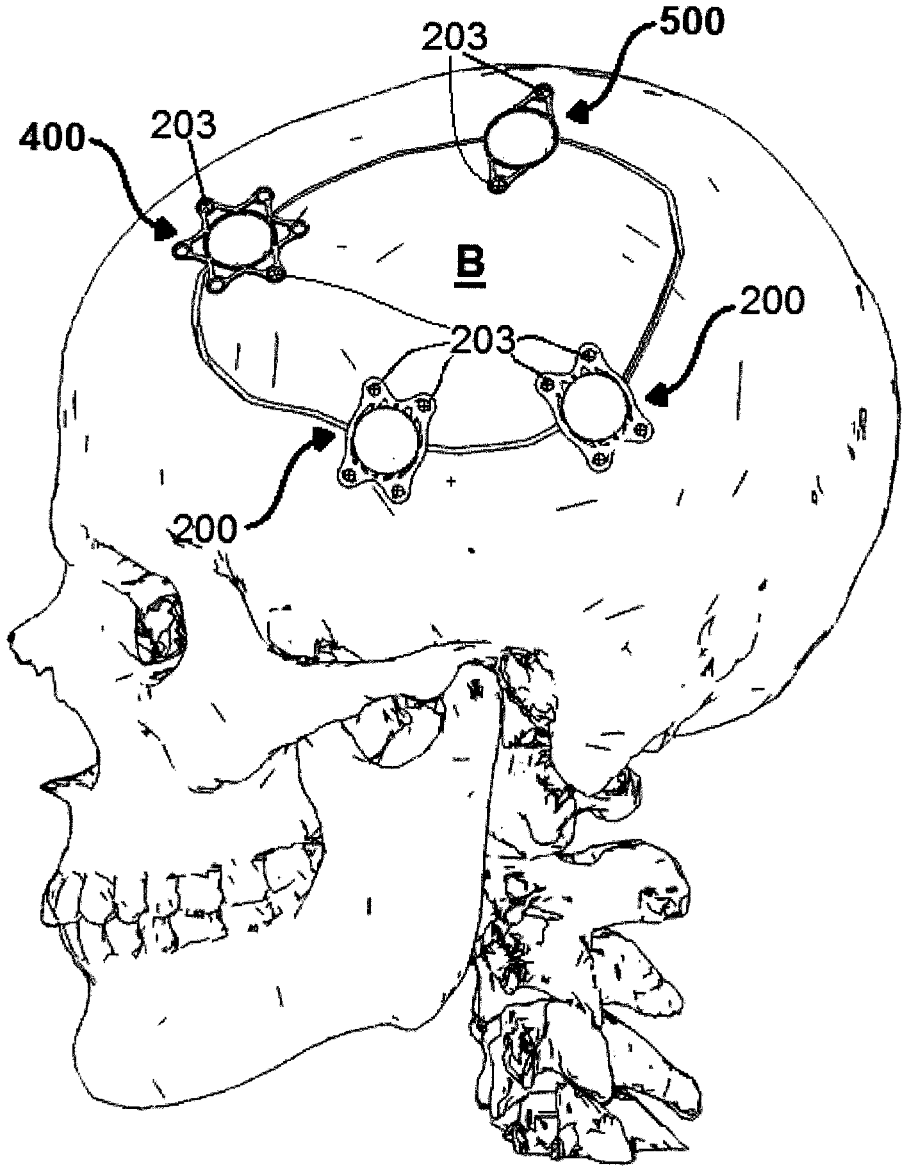
FIG. 47 depicts a bone flap (B) reattached to a skull using two of the bore hole implants (200) of FIGS. 17-23, a bore hole implant (400) of FIGS. 27-36, and a bore hole implant (500) of FIGS. 37-46, wherein each implant is anchored in place using at least one bone screw driven through a retention eyelet of the implant into the bone flap and at least one bone screw driven through a retention eyelet of the implant into bone adjacent the outer perimeter of the bone flap.

The present disclosure provides bore hole implants for filling a bore hole (also referred to as a burr hole) in bone, including those formed in a skull during various surgical procedures. For example, when it is necessary to remove a portion of a patient's skull, two or more (typically three) bore holes are created. The bore holes are then joined by saw cuts that together with the bore holes form a continuous cut line through the skull, thereby releasing a bone flap that is lifted to allow access to the underlying tissue. The implants (100, 200, 300, 400, 500) described herein can be used to anchor the bone flap back in place after completion of a surgical procedure, as well as to at least partially fill the bore holes. For example, FIG. 47 depicts the reattachment of a bone flap (B) using four implants (200, 400, 500) according to the present disclosure. The implants of the present disclosure are also adapted for at least partially filling a bore hole made in a patient's skull for other purposes, such as individual bore holes made, for example, to allow for the insertion of drainage tubes for draining a subdural hematoma (e.g., a singular bore hole created in a patient's skull).

The bore hole implants of the present disclosure generally comprise a biocompatible plate and a support structure having inner and outer support frames. The inner support frame is partially embedded in the plate, and includes an annular portion that extends around an upper periphery of the plate. In some embodiments, another portion of the inner support frame extends from the annular portion into the plate in order to provide additional strength and maintain the integrity of the plate. The inner support frame and plate are configured to be positioned within a bore hole, with the outer support frame adapted for securing the implant in place.

The inner support frame generally comprises a ring-shaped member (e.g., an annular ring) having an outer surface (e.g., a surface of revolution such as a cylindrical surface) that defines the outer diameter of the inner support frame, wherein that outer diameter is greater than the outer diameter of the plate. The ring-shaped manner is arranged so as to extend around the outer circumference of the plate, at or near the upper peripheral edge of the plate, with the outer surface of the ring-shaped member exposed (i.e., not covered by the plate material). In this manner, the outer surface of the ring-shaped member protects the outer circumference of the plate from being damaged prior to insertion into a bore hole. In some embodiments (e.g., FIGS. 1-26) the ring-shaped member of the inner support frame provides a protective ring having an outer diameter that can be precisely sized so as to at least partially fit within a bore hole. In alternative embodiments (e.g., FIGS. 27-45), the ring-shaped member is configured to remain outside of the bore hole, covering the outer perimeter of the bore hole.

The outer support frame is connected to the exposed outer surface of the inner support frame, and is adapted for securement to bone surrounding the bore hole after the plate and ring-shaped member have been inserted into a bore hole. The outer support frame thus includes retention features in the form of a plurality of fastening points. In some embodiments, the fastening points comprise eyelets through which fasteners (e.g., bone screws or sutures) can be inserted in order to attach the implant to bone surrounding a bore hole. By way of example, bone screws can be driven through the retention eyelets into the bone. In some embodiments, the outer support frame can be adjusted (e.g., portions bent or otherwise deformed) in order to, for example, match the shape of the patient's bone surrounding a bore hole, and/or to position the fastening points at a desired location and/or in a desired orientation. Thus, in some embodiments elements of the outer support frame are deformable (e.g., include one or more deformation zones) so that the support structure can be adjusted for optimal fit. By attaching the outer support frame to the exposed outer surface of the inner support frame, the elements (e.g., struts) that connect the outer support frame to the inner support frame can be deformed to allow for adjustment of the outer support frame without risk of cracking the plate material.

The outer support frame generally includes at least two fastening points (e.g., retention eyelets) arrayed around, and spaced away from the inner support frame and the plate. By way of example, two, three, four, five, six, seven or even eight retention eyelets can be arranged about the inner support frame and plate in a variety of patterns. In some embodiments, adjacent eyelets are connected by wire members such that two wire members extend from each eyelet so as to connect the eyelets to one another. In such arrangements, the wire members and eyelets encircle, and are spaced away from, the inner support frame. These wire members are attached directly to the outer surface of the ring-shaped portion of the inner support frame, or are attached thereto by struts. In other embodiments, each eyelet is connected to the inner support frame (e.g., to the outer surface of the ring-shaped portion of the inner support frame) by one or more (e.g., two) wire members, which are themselves attached directly to the outer surface of the ring-shaped portion of the inner support frame or are attached thereto by struts (e.g., implant (500)).

In some embodiments, the inner diameter of the ring-shaped member is controlled such that the ring-shaped member encircles the outer circumference of the plate, with the plate material covering the inner surface of the ring-shaped member (i.e., a portion of the ring-shaped member is embedded within the plate). In still further embodiments, the inner diameter of the ring-shaped member is slightly smaller than the outer circumference of the plate (at least at the intersection of the plate and the ring-shaped member) such that the inner surface of the ring-shaped member as well as a portion of the upper surface (and optionally a portion of the bottom surface) of the ring-shaped member are covered by the plate material.

The inner support frame of some embodiments also includes one or more support members that are connected to and extend inwardly away from the inner surface (e.g., an inner surface of revolution such as a cylindrical surface) of the ring-shaped member such that the support members are embedded within the plate. In some embodiments, the support members extend inwardly across the interior of the inner support frame such that the support members, either alone or collectively, span across the interior of the plate. In other embodiments, the support members only extend partially across the interior of the ring-shaped member such that no support member intersects the central axis of the plate. The support members provide additional strength and rigidity to the inner support frame, as well as maintain the integrity of the plate (e.g., prevent, or limit the extent of, cracking of the plate), while still allowing the biocompatible plate to be molded (or otherwise formed) over and about the inner support frame so as to fill the interior of the ring-shaped member of the inner support frame.

Some plate materials, particularly cement compositions, often have a tendency to fracture along planes. Therefore, in some embodiments the support members are configured such that they do not extend from the inner surface of the ring-shaped member into the plate along a single plane-particularly one that is orthogonal to the central axis of the plate. For example, in some embodiments one or more support members are provided that extend inwardly from the inner surface of the ring-shaped member, wherein at least a portion of each support member extends from the inner surface of the ring-shaped member at an angle with respect to a plane that is orthogonal to the central axis (L) of the plate (e.g., an angle greater than 0° and less than 20°, or between 0.5° and 15°). Thus, the depth of the support members within the plate varies along their lengths. Since the plurality of angled support members extend inwardly from the inner surface of the ring-shaped member from locations arrayed about the inner surface, such support members will not lie in the same plane even if they extend at the same angle with respect to the central axis of the plate. In other instances, the support members are curved along at least a portion of their lengths, such that their angle with respect to the central axis of the plate varies along the length of the support member. For example, the support members can curve downwardly as they extend from the inner surface of the ring-shaped member into the plate, thereby preventing the formation of a potential fracture plane at the interface between the support members and the plate material.

In addition (or as an alternative to angled or curved support members), the support members can be textured, thereby providing an uneven surface that not only improves cement adherence to the support members, but also helps prevent fracturing of the cement along a fracture surface extending along the support members. Such texturing can be in the form of, for example, a plurality of protrusions and/or depressions in the surface, and/or a roughened rather than smooth surface for the support members. Other surfaces of the inner support frame (e.g., the inner surface of the ring-shaped member) can similarly be textured so that the surface contacting the plate material is not smooth.

In some embodiments of the present disclosure, the bore hole implant comprises (a) a biocompatible plate having an upper surface, a bottom surface, a central axis, and an outer surface of revolution around said central axis; and (b) a support structure. The support structure includes: an inner support frame that includes a ring-shaped member encircling the plate, and at least one support member connected to and extending inwardly from the inner surface of the ring-shaped member within the plate; and an outer support frame comprising a plurality (e.g., 2, 3, 4, 5, 6, 7, or 8) of fastening points adapted for attaching the implant to bone surrounding a bore hole in which the plate is inserted. The ring-shaped member has an exposed outer surface defining the outer diameter of the ring-shaped member and an inner surface defining the inner diameter of the ring-shaped member, while the outer support frame is connected to and extends away from the outer surface of the inner support frame. By way of example, the outer support frame's fastening points, in the form of retention eyelets, can be connected to the exposed outer surface of the ring-shaped member by: wire members, which can optionally extend between adjacent eyelets, wherein the wire members are connected to the outer surface of the ring-shaped member (e.g., by one or more struts); and/or by struts. At least a portion of the support member(s) extends inwardly from the inner surface of the ring-shaped member at an angle with respect to a plane that is orthogonal to the central axis of the plate such that the depth of the support member(s) within the plate varies along its length. As noted above, this avoids the formation of a potential fracture plane at the interface between the support members and the plate material. For example, each of the support members can extend downwardly into the plate such that the lowermost edge of each support member is spaced away from the bottom of the plate by a distance that is less than 50%, less than 40%, less than 30% or less than 20% of the maximum thickness of the plate.

In some embodiments, each of said support members extends inwardly and downwardly from the inner surface of the ring-shaped member such that the support members are curved along at least a portion of their lengths. By way of example, each of the support members can be in the form of a wire loop having first and second connected legs, the first leg extending inwardly and downwardly away from a first portion of the inner surface of the ring-shaped member, and the second leg extending inwardly and downwardly away from a second portion of the inner surface of the ring-shaped member, with the intersections of the first and second legs with the inner surface of the ring-shaped member spaced apart (e.g., U-shaped support members). Each of these support members can further include an inner segment that connects the first and second legs, with the inner segments spaced inwardly away from the inner surface of the ring-shaped member. In some instances, the width of each inner segment is greater than the width of the first and second legs connected thereto.

In some instances, each of the support members extends radially inward from the inner surface of the ring-shaped member a distance that is less than one half the maximum diameter of the plate. Thus, when the inner support frame includes a plurality of support members, the support members can be configured such that they do not contact each other within said plate. In addition (or alternatively), the support members can also be configured such that no portion of the support members intersects the central axis of the plate. This can be advantageous in that it reduces the weight of the implant (as well as the amount of metal or other support structure material needed). If desired (e.g., to allow for greater manipulation of the location of the retention features), each of the support members can include a region of reduced cross-section located adjacent the inner surface of the ring-shaped member so as to provide deformation zones. When the ring-shaped member is fabricated from sheet material (e.g., titanium or titanium alloy) such as by cutting or stamping, these deformation zones allow the support members to be deformed into the desired angled (including curved) orientation with respect to the plate.

As used herein, the term "wire" refers to a strand, rod, strut, or similar structure having a length that is relatively long compared to its width and thickness, regardless of cross-sectional shape. For example, a "wire," as used herein, can have a circular, oval, rectangular, or other cross-sectional shape. In some of the embodiments described herein, certain wires of the implants do not have a constant width and/or thickness along their entire length, and may have segments or regions that are irregular in shape. For example, some wires may have a pleated segment that allows the effective length of the wire to be elongated or shortened, while others have segments of reduced width and/or thickness to provide regions of greater flexibility. In other embodiments, one or more wires have segments of increased width and/or thickness in order provide greater rigidity and/or support to the implant. An individual wire may be in the form of a single, continuous structure, or a plurality of individual filaments or strands may be combined to form a wire (e.g., wrapped or braided).

The various materials suitable for use in fabricating the support structure and biocompatible plate will be described in detail later. Each can be made from any of a variety of biocompatible materials suitable for implantation in a patient. For example, the support structure may be manufactured from various metals (e.g., titanium or titanium alloy), polymers, or even composite materials of two or more metals and/or polymers. The biocompatible plate can be composed of any of a variety of resorbable and/or stable (i.e., non-resorbable) biocompatible materials suitable for implantation in a patient, including various types and/or combinations of polymers, ceramics and metals. In some embodiments, the biocompatible plate is composed of a moldable bioceramic or biopolymer material, such as a hydraulic cement composition from which the plate is molded onto the inner support frame (as further detailed herein), and the support structure cut or stamped from titanium or titanium alloy.

Figure 6:
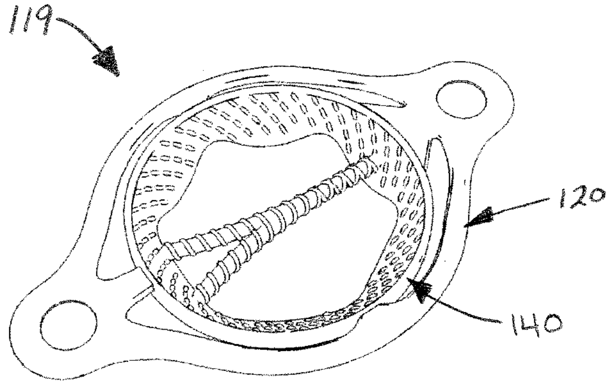
FIG. 6 depicts a perspective view of the support structure of the implant of FIG. 1, comprising inner and outer support frames.
Figure 7:
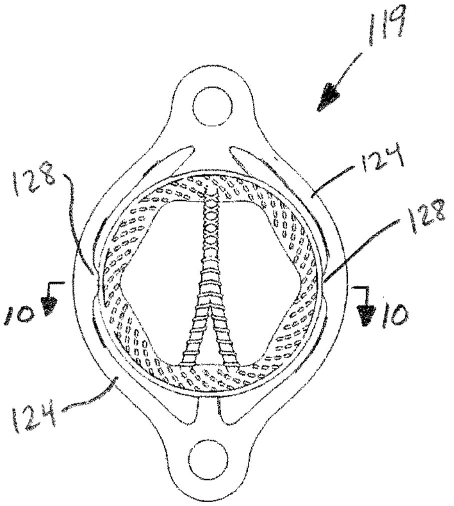
FIGS. 7-9 depict a top plan view, side view and bottom plan view, respectively, of the support structure of the implant of FIG. 6.
Figure 8:
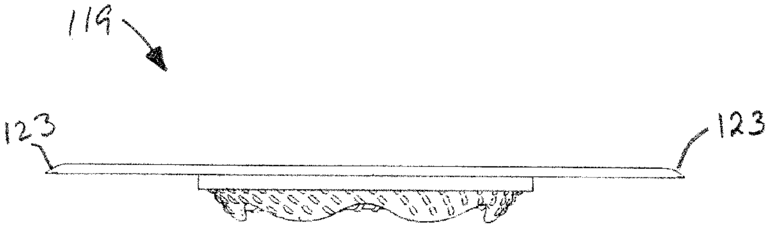
Figure 9:
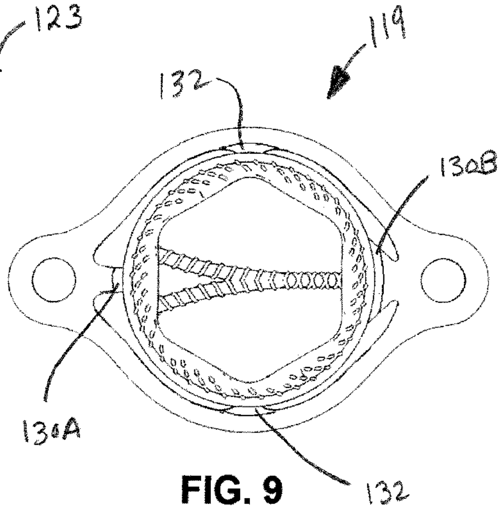

FIGS. 1-16 depict one embodiment of a bore hole implant (100), which generally comprises a biocompatible plate (112) and a support structure (119) comprising an outer support frame (120) and an inner support frame (140) (see FIG. 6). Only a portion of inner support frame (140) is visible in FIGS. 1-5, as the remainder is embedded within the plate (112). As used herein, "embedded" means that the structure or surface in question is covered by the plate material and is therefore not visible.

Figure 14:
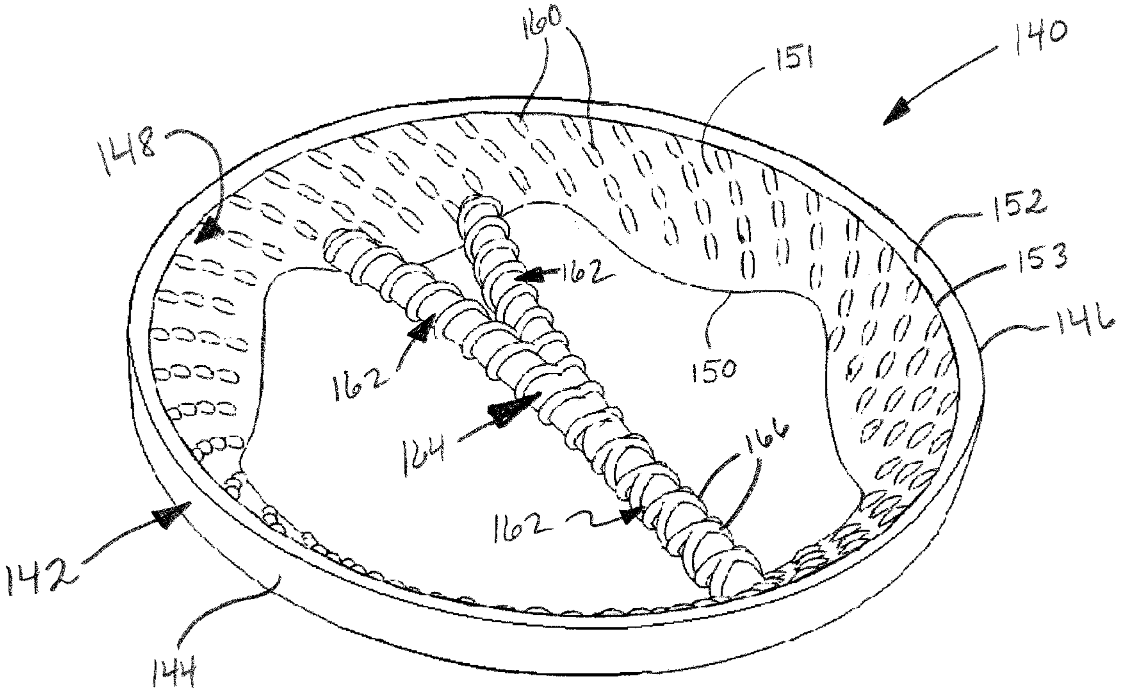
FIGS. 14 and 15 depict top and bottom perspective views, respectively, of the inner support frame of the support structure of FIG. 6, wherein the outer support frame has been removed for clarity.
Figure 15:
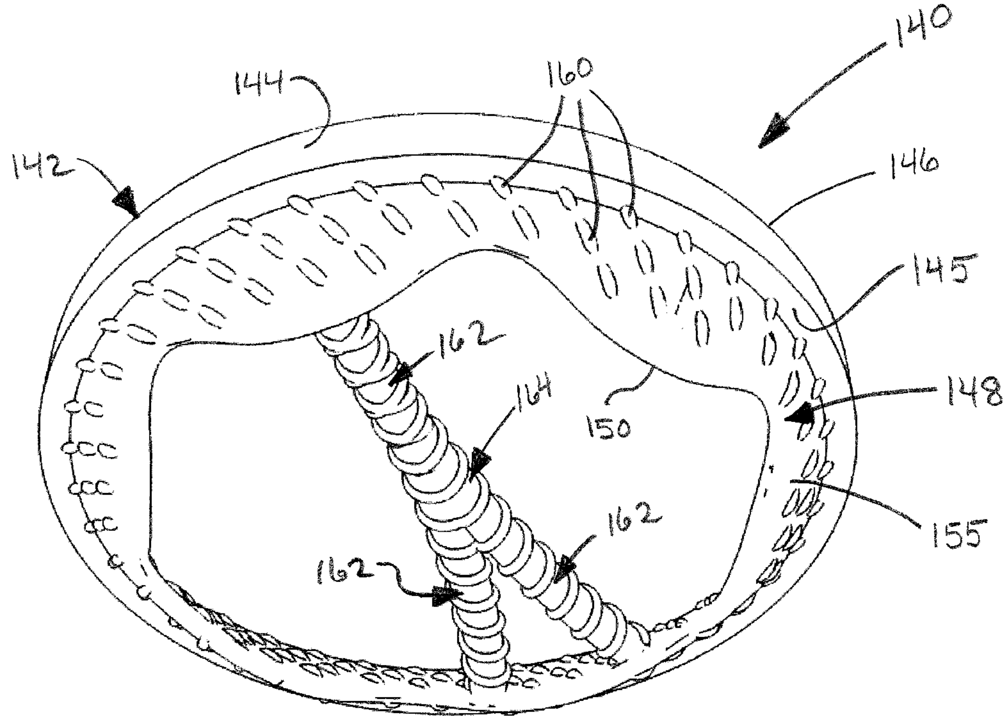
Figure 16:
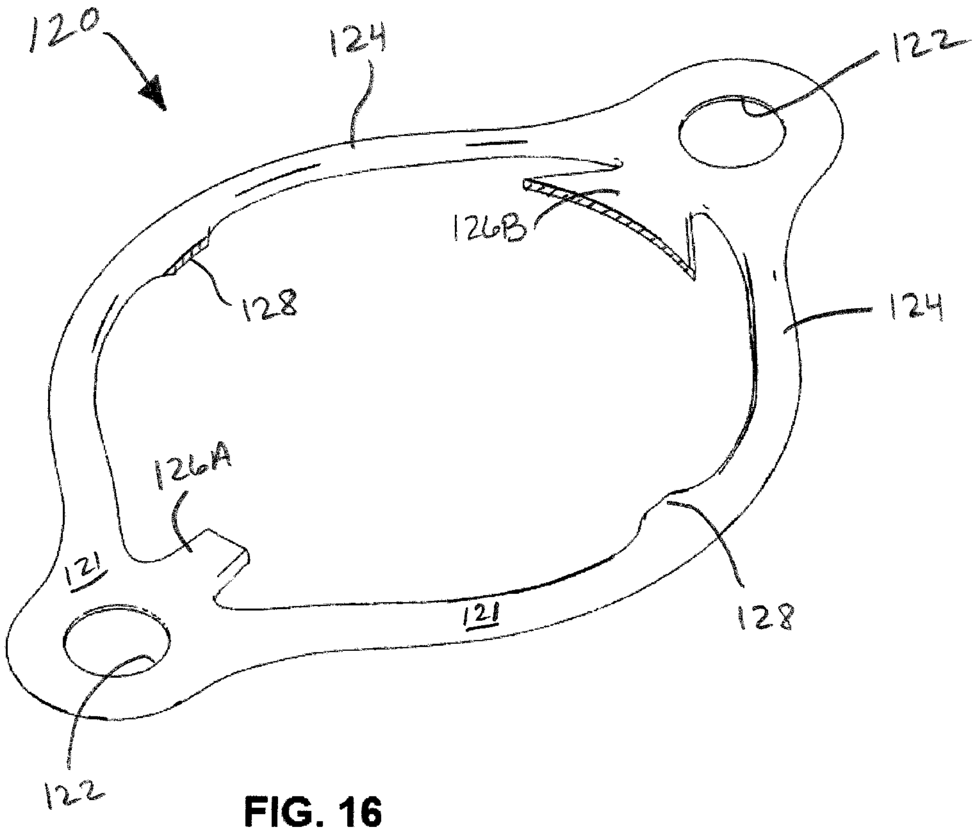
FIG. 16 depicts a perspective view of the outer support frame of the support structure of FIG. 6, wherein the inner support frame has been removed for clarity.
Figure 17:
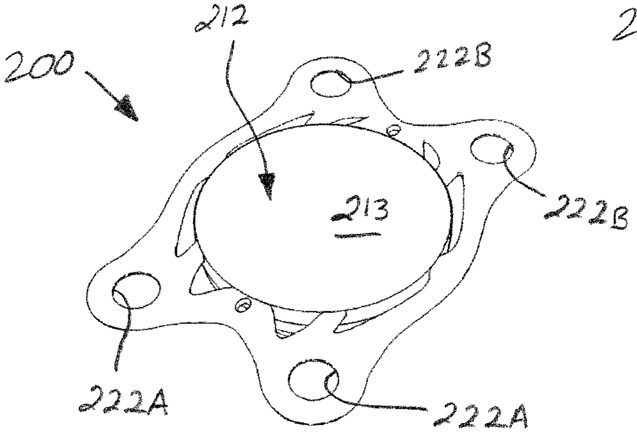
FIG. 17 is a perspective view of an alternative embodiment of a bore hole implant.
Figure 18:
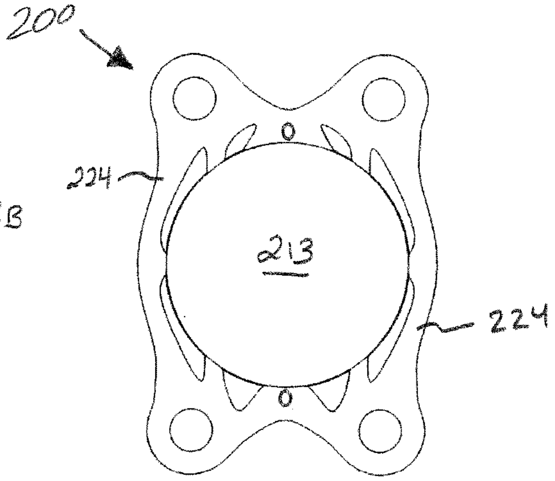
FIGS. 18-21 depict a top plan view, side view, bottom plan view, and bottom perspective view, respectively, of the implant of FIG. 17.

Specifically, only an outer surface (144) of the inner support frame (140) is visible in FIGS. 1-5. In this embodiment, the outer surface (144) is a surface of revolution, in this specific instance a cylindrical outer surface (144). It will be understood that, as used herein, a "cylindrical surface" includes not only right cylinder surfaces such as depicted for outer surface (144), but also tapered cylinder surfaces—i.e., the outer diameter of surface (144) can taper slightly through its height (e.g., a frustoconical surface when the taper is constant). FIGS. 6-11 and 13 depict the support structure (119) in more detail, with the plate (112) omitted for clarity. FIGS. 14 and 15 depict inner support frame (140) with the outer support frame (120) and plate (112) omitted in order to better depict the configuration of the inner support frame. FIG. 16 depicts the outer support frame (120) alone, with the inner support frame (140) and plate (112) omitted.

Figure 3:
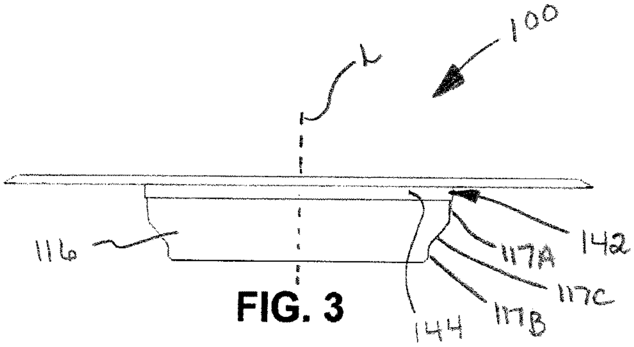
Figure 5:
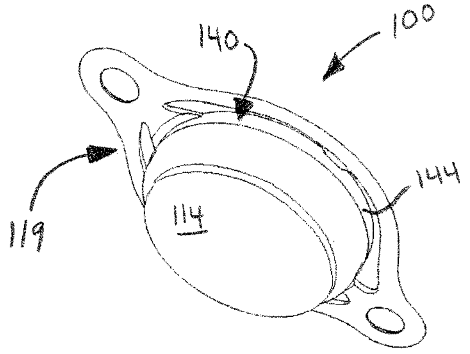
Figure 4:
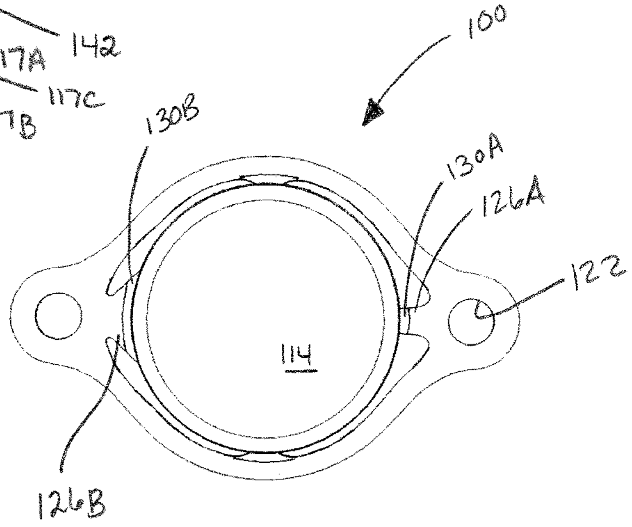

Plate (112) has an upper surface (113), a bottom surface (114), a central axis (L), and a sidewall (116) comprising a surface of revolution about the central axis (L). Thus, plate (112) has a circular cross-section through any plane perpendicular to its central axis (L). In the particular embodiment shown, the diameter of the plate (112) tapers such that its diameter is smallest adjacent the bottom surface (114) and is largest adjacent the top surface (113). The shape of sidewall (116) of plate (112) generally corresponds to the shape of a bore commonly made with a cranial perforator, and, as shown in FIG. 3, includes an upper cylindrical section (straight or tapered cylinder) (117A), a lower cylindrical section (straight or tapered cylinder) (117B), and a curved transition segment (117C) extending therebetween. Thus, sidewall (116) has a shape, when viewed in cross-section, approximating an ogee or sigmoid curve. In the embodiment shown, the diameter of the upper cylindrical section (117A) tapers slightly in order to facilitate not only removing the plate (112) from its mold, but also the insertion of the plate (112) into a bore hole in a patient's skull. It will be understood that the plate (112) can have any of a variety of other shapes, such as that of a straight or tapered cylinder, or even an oval, triangular, square, rectangular, pentagonal, hexagonal, etc. cross-sectional shape. However, in most instances a plate having an outer surface of revolution about a central axis will most closely match the shape of a bore hole created by a rotating perforator/drill, thereby allowing the plate (112) to be snugly urged into a bore hole.

Support structure (119) (see FIGS. 6-13) comprises an outer support frame (120) connected to and spaced away from an inner support frame (140). Inner support frame (140) is a ring-shaped structure, comprising an annular flange (142) having a cylindrical outer surface (144) and an upper edge (146) (see FIGS. 14-15). The inner support frame further includes a sidewall (148) extending circumferentially about the inner support frame (140) and downwardly from the flange (142) thereof, terminating in a lower edge (150). The sidewall (148) is thus annular in nature. It will be understood, however, that, since sidewall (148) is embedded in the plate (112) of the implant (as described below), sidewall (148) as well as the various other features located within plate (112) of the fabricated implant (100) can be of any of a variety of other shapes besides those described and depicted herein. For example, sidewall (148) can comprise a circular, oval or polygonal (e.g., hexagonal, pentagonal, etc.) ring-shape. The sidewall (148) reinforces the plate and provides mechanical stability.

In the embodiment shown, the sidewall (148) is also angled inwardly, such that the portion of the inner support frame (140) below the flange (142) is tapered in diameter. As a result, the inner surface (151) of the sloped sidewall (148) is annular in nature, extending upwardly from the lower edge (150) to the upper surface (152) of the inner support frame. In other embodiments described herein, the inner surface of the ring-shaped inner support frame is not angled (or is only slightly angled, e.g., less than 45°, less than 35°, or less than 20°) and therefore presents an inner cylindrical surface. The upper surface (152) of the inner support frame (140) is itself sloped inwardly, as best seen in the cross-sectional views of FIGS. 10-11. However, the degree of inclination of upper surface (152) with respect to a plane that includes the central axis (L) is less than that of sidewall (148) (i.e., upper surface (151) is slightly less sloped inwardly than sidewall (148)). Alternatively, the upper surface (152) can be flat (i.e., orthogonal to a plane that includes the central axis (L)). Upper surface (152) extends between the upper interior edge (153) of sidewall (148) to upper edge (146) of the inner support frame (140) (see FIG. 13).

The lower edge (150) of sidewall (148) is irregular such that the length of sidewall (148) (i.e., from upper interior edge (153) to lower edge (150)) varies about its circumference. The variability in length can be ordered (as shown) or random. In the depicted embodiment, the lower edge (150) is irregular such that the length of sidewall (148) generally varies between a maximum and minimum in a repeating pattern. Thus, the lower edge (150) is approximately sinusoidal in shape. By varying the length of sidewall (148) and thereby providing an irregular lower edge (150), fracturing of the plate along a plane corresponding to the lower edge (150) of the sidewall can be avoided. Thus, it will be understood that the approximately sinusoidal shape of lower edge (150) is merely exemplary, as a variety of other irregular shapes may be employed-particularly wherein the lower edge (150) is non-planar in any direction (i.e., the lower edge (150) is not flat in any cross-section). In alternative embodiments, the lower edge (150) is planar (e.g., the entirety of the lower edge (150) lies in a plane that is orthogonal to a plane that includes the central axis (L)).

In some embodiments the inner surface (151) and/or outer surface (155) of sidewall (148) is textured (i.e., non-smooth), thereby providing an uneven surface that not only improves cement adherence to the sidewall (148), but also helps prevent fracturing of the cement along a fracture surface extending along sidewall (148). Such texturing can be in the form of a plurality of protrusions and/or depressions in the surfaces. In the particular embodiment depicted, a plurality of protrusions (160) in the form of bumps is provided on both the inner surface (151) and outer surface (155) of sidewall (148). Of course, other forms of protrusions can be employed such as ridges, bumps in combinations with ridges, and similar types of texturing. Additionally or alternatively, one or more of the plate-contacting surfaces can be roughened in order to provide a textured, non-smooth surface.

The inner support frame (140) in the depicted embodiment also includes an interior support structure comprising one or more support members (162). Support members (162) extend inwardly across the interior of the inner support frame between portions of inner surface (151) of sidewall (148). The support members (162) provide additional strength and rigidity to the inner support frame (140), while still allowing the biocompatible plate to be molded over and about the inner support frame so as to fill the interior of the inner support frame. In the depicted embodiment, three such support members (162) are provided, and are joined to one another at a juncture (164) spaced inwardly of the sidewall (148), at or near the central axis (L) of the implant (i.e., at or near the center of the interior of the support structure (119)). It will be understood, however, that any number and arrangement of support members extending across the interior of the inner support frame (140) may be provided. In some embodiments, the support members (162) are also angled with respect to the axis of the plate. For example, in some embodiments a plurality of support members are provided that extend inwardly from the inner surface of the ring-shaped member at an angle with respect to a plane that is orthogonal to the central axis (L) of the plate (e.g., an angle greater than 0° and less than 20°, or between 0.5° and 15°). As a result, the depth of the support members (162) within the plate (112) (e.g., with respect to the top surface or the bottom surface of the plate) is not constant.

The support members (162), like sidewall (148), are optionally textured, thereby providing an uneven surface that not only improves cement adherence to the support members (162), but also helps prevent fracturing of the cement along a fracture surface extending along the support members (162). Such texturing can be in the form of a plurality of protrusions and/or depressions in the surfaces. In the depicted embodiment, protrusions in the form of one or more spiral ridges (166) are provided on the support members (162).

Outer support frame (120) comprises a plurality of fastening points adapted for attaching the implant to bone surrounding a bore hole. In the embodiment shown, a pair of fastening points in the form of retention eyelets (122) is provided. The retention eyelets (122) are adapted to receive a fastener therethrough, such as a bone screw, suture or other fastener known to those skilled in the art. Retention eyelets (122) are located at opposite ends of the implant (100) such that an imaginary line (M) intersecting the centers of retention eyelets (122) also intersects the central axis (L) of the implant (100) (see FIG. 2). It will be understood, however, that any number of eyelets (122) or other fastening points can be provided, at any of a variety of locations about the periphery of, and spaced away from, the biocompatible plate (112).

It should be noted that, as used herein, the term "eyelet" means an opening having a closed or partially closed (e.g., >60%, >70%, >80% or >90%) perimeter, but it is not limited to a particular shape. Thus, eyelets (122) can be round, square, rectangular, trapezoidal, hexagonal, tear-drop, oval, elliptical or any other suitable shape. Of course, other types of attachment apertures or other fastening points may be used in place of, or in addition to the eyelets (122). Also, while the eyelets of the implants (100, 200, 300, 400, 500) described herein are depicted as being entirely closed (i.e., form complete circles), it will be understood that the term "eyelet," as used herein, includes semi-annular structures that are only partially closed, such as C-rings (e.g., open loop 1019' in FIG. 11*a*) of the '900 App. (U.S. Pub. No. 2013/0053900A1).

The outer support frame (120) further includes a pair of wire members (124), each of which extends between the retention eyelets (122) along opposite sides of the implant (100). Thus, the wire members (124) and the eyelets (122) encircle, and are spaced away from, the outer surface (144)

of the inner support frame (140) such that a gap is provided between wire members (124) and the inner support frame (140).

The outer support frame (120) is connected to the inner support frame (140) by a plurality of struts (126, 128). An end strut (126A, 126B) extends between and connects each retention eyelet (122) and outer surface (144) of the inner support frame, with the end struts (126A, 126B) located at opposite ends of the implant (100)). Along both sides of the implant, intermediate the retention eyelets (122), a side strut (128) extends between and connects each wire member (124) and outer surface (144) of the inner support frame (140). The struts, which, in the embodiment shown, are thinner than the height of the outer surface (144), connect to the outer surface (144) such that the upper surface of the struts (126, 128) is generally flush with the upper edge (146) of the inner support frame (140) (see FIG. 13). In the depicted embodiment, end strut (126B) is wider than end strut (126A) and increases in width towards flange (142) in order to provide additional strength during fabrication of the support structure (119), particularly when the support structure is fabricated by additive manufacturing techniques such as selective laser sintering or selective laser melting. Any number of struts (126, 128) extending between and connecting the outer frame to the outer surface (144) of the inner frame can be provided. Thus, the number, shape and location of such struts may be varied, as desired.

In order to secure the implant (100) in a bore hole or other bone defect, the plate (112) is alignably positioned within the bore hole. In addition, a portion of the exposed outer surface (144) of the inner support frame is inserted into the bore hole, with the bottom surfaces of the retention eyelets (122) and wire members (124) located against the surface of the bone surrounding the bore hole. The implant is then secured to bone surrounding the bone defect, such as by bone screws urged into the bone through the retention eyelets (122). As a result, the implant is secured in place, with the plate firmly located in, and filling, the bore hole. The other implant embodiments (200, 300, 400, 500) described herein are implanted in a bore hole in the same manner (although with the implants (400, 500) no portion of the inner support frame is received within the bore hole). In embodiments having more than two fastening points, in some instances it may not be necessary to use all of the fastening points to secure the implant in place. For example, as seen in FIG. 47, implant (400) is secured in place using only two bone screws (203) and two of six retention eyelets-one bone screw is used to secure the implant to the bone flap (B) and the other bone screw is used to secure the implant to the bone adjacent the bone flap.

Since the bone surrounding a bore hole is usually curved to varying degrees and often in more than one direction, it will often be necessary or desirable to bend portions of the outer support frame in order to orient the retention eyelets (122) and wire members (124) such that their bottom surfaces will lie flat (or nearly flat) against the bone. This not only minimizes any gaps between the support frame and surrounding bone, but also helps to ensure that a screw or other fastener driven through the eyelets into the surrounding bone will have sufficient purchase. For example, since the retention eyelets in the embodiment shown in FIGS. 1-16 extend away from the outer ends of the wire members (124), the eyelets can be deformed (i.e., bent) where the eyelets intersect the wire members in order to facilitate a more secure attachment to the surrounding bone since the eyelets can be manipulated so as to lay flush (or nearly flush) against the outer surface of the bone.

In addition, particularly when a greater repositioning of one or more eyelets is required so as to better match surrounding bone as well as to position the bottom surfaces of the wire members to lie as flat as possible against the surrounding bone, portions of one or more of the wire members (124) and struts (126, 128) can be bent so that one or more of the retention eyelets and/or wire members can be better oriented with respect to the bone surrounding a bore hole. Because the wire members (124) and struts (126,128) connect the inner and outer support frames external to the plate (112) (i.e., at outer surface (144)), the wire members and struts can be deformed (i.e., bent) without risk of cracking the plate.

Portions of the eyelets (122), wire members (124) and/or struts (126, 128) can be bent upwardly and/or downwardly, as necessary. For example, prior to implantation in a patient, portions of one or more of the eyelets can be bent upwardly so as to orient the retention eyelets (122) at an angle less than 180° with respect to the plane of the upper surface (113) of the plate (112). Such bending may be necessary, for example, when the implant is to be inserted into a bore hole located in or immediately adjacent to a concavely curved surface of a patient's skull (e.g., a bore hole in the sphenoid bone immediately adjacent the zygomatic bone). Of course, the eyelets, wire members and/or struts can be bent in any of a variety of directions (e.g., upwardly or downwardly) and degrees so as to better match the surface of the bone surrounding a bore hole, and without cracking the plate (112).

In order to further facilitate deformation of the outer support frame, in some embodiments deformation zones are provided on one or more portions of one or more of the struts (126, 128). As used herein, the term "deformation zone" means a region of a structure that is adapted to facilitate deformation of that region, such as by bending (including twisting or flexing), stretching and/or compression. Deformation zones include regions of a structure, particularly the struts (126, 128) which have a reduced cross-section (e.g., reduced width and/or reduced thickness), or otherwise have reduced rigidity, as compared to adjacent regions of that structure, such that, when a deforming force is applied, the structure will tend to deform (e.g., bend) at the deformation zone rather than in an adjacent region. Deformation zones in the implants described herein can comprise, for example, regions of reduced cross-section—whether that reduced cross-section is a result of a reduction in width, thickness and/or diameter—as well as pleated regions.

Figure 10:
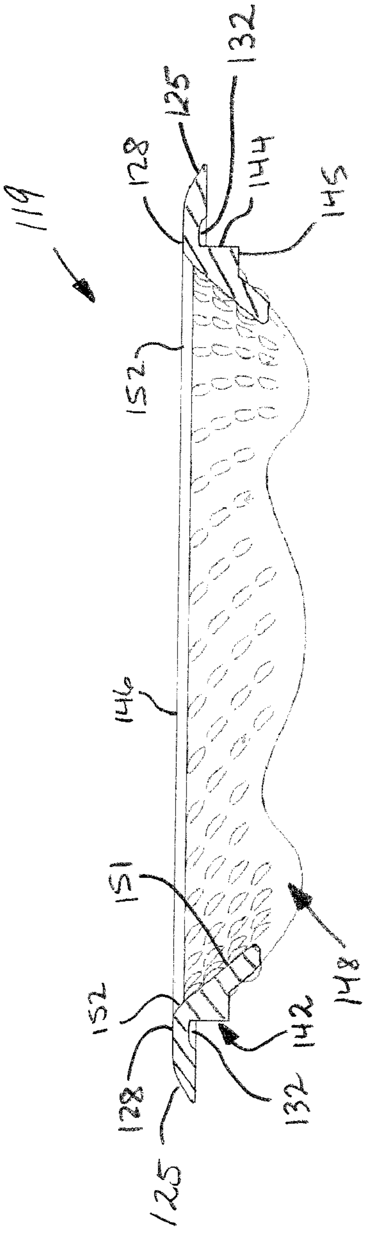
FIG. 10 is a cross-sectional side view of the support structure of FIG. 7, taken along the line 10-10 thereof, wherein the internal support members of the inner support frame have been removed for clarity.
Figure 11:
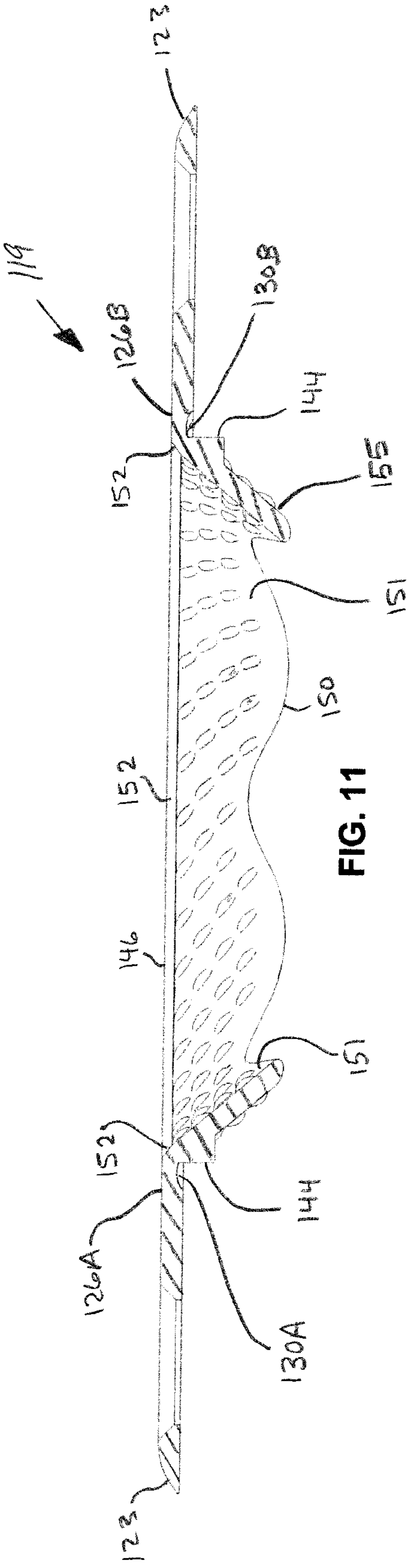
FIG. 11 is a cross-sectional side view of the support structure of FIG. 10, rotated 90 degrees from the view of FIG. 10.

In the embodiment shown in FIGS. 1-16, each strut (126, 128) includes a deformation zone comprising a reduced-thickness region (130A, 130B, 132) adjacent to the outer surface (144) of the flange (140), as best seen in FIGS. 10 and 11. Each reduced-thickness region (130A, 130B, 132) comprises a notch extending upwardly from the bottom surface of the strut (126, 128), located immediately adjacent outer surface (144) of the inner support frame (120). In other words, the struts (126, 128) are thinnest where they meet the outer surface (144). The reduced-thickness regions (130A, 130B, 132) also span the entire width of their respective struts (126, 128), and are generally curved (about the central axis (L)) so as to match the curvature of the outer surface (144). The deformation zones provided by the reduced-thickness regions (130A, 130B, 132) allow the outer support frame to be adjusted by bending or other manual manipulation prior to implantation in order to orient the retention eyelets and wire members so that their bottom surfaces will lie as flat as possible against the bone.

In addition, the deformation zones also facilitate deformation (e.g., bending) of the struts (126, 128) from the forces applied to the eyelets as screws (or other fasteners) are driven through the eyelets into bone during implantation. While one or more of the eyelets and portions of the wire members or struts may not lie flush against the bone when the implant is first inserted into a bore hole, as the implant is secured to bone (e.g., using a screw driven into bone through the eyelet) the bottom surface of the eyelet, as well that of the associated strut (126A, 126B) and adjacent regions of the wire members (124), will be pulled towards the bone. In many instances, this will result in a bending force that causes one or more of the struts to bend at their deformation zones. Thus, bending forces, whether applied manually or as a result of securement of the implant to bone, will cause one or more of the struts (126, 128) to bend at their deformation zone, exterior to the plate (112), thereby preventing cracking of the plate (112).

In addition to or in place of the reduced-thickness regions (130, 132), deformation zones in the form of pleated regions may also be provided on one or more of the struts and/or wire members (124). Such pleated regions would include one or more pleats which allow additional deformation of the outer support frame, and may optionally have a reduced cross-section (e.g., reduced width and/or reduced thickness) compared to the surrounding portions of the strut or wire member on which the pleats are provided. Such pleated regions not only facilitate deformation of the outer support frame, but also allow the pleated regions of the outer support frame to be locally stretched or compressed in order to further facilitate shaping of the implant to match a patient's skull or other bone, as well as repositioning of the eyelets.

It will be understood that the implant (100) may be modified such that deformation zones are not provided on all of the struts (126, 128). As yet another alternative, reduced-thickness regions may be configured to comprise a notch or other recess that extends downwardly from the upper surface of the strut, instead of or in addition to one that extends upwardly from the bottom surface of the strut. Furthermore, deformation zones comprising reduced-width regions may be provided on the struts, instead of or in addition to the reduced-thickness regions. Likewise, deformation zones of the various types described above also may be provided on one or more of the wire members (124) and/or on portions of one or more of the eyelets (122) (i.e., on the material forming the perimeter of the eyelets).

In some instances it is desirable to minimize the thickness of the outer support frame, not only to facilitate the deformation of the outer support frame (120) as described above, but also because the outer support frame will rest on the surface of the bone following implantation. Thus, in order to obtain good aesthetical results and minimize patient discomfort, in some embodiments the thickness of the outer support frame is as small as possible while still maintaining sufficient strength. Accordingly, in the embodiment of FIGS. 1-16 and as best seen in FIG. 3, the thickness of the outer support frame is less than the height of the outer surface (144) of the inner support frame (140). In one embodiment, the outer support frame has a thickness of about 0.2 to about 0.6 mm, or about 0.3 to about 0.45 mm. And the outer surface (144) of the inner support frame (140) has a thickness of about 0.5 to about 1.3 mm, or about 0.6 to about 1.0 mm.

In some embodiments, the outer periphery of the outer support frame is also tapered such that the outer support frame is thinnest at its outer perimeter. This is best seen in FIGS. 10 and 11, wherein the outer periphery (125) of the wire members (124) as well as the outer periphery (123) of the retention eyelets are tapered such that the wire members and retention eyelets are thinnest at their outer edges. This tapering improves implant fit and aesthetics by providing a smooth, reduced height transition between the surface of surrounding bone and the upper surfaces of the implant. By way of example, in some embodiments the outer edges of the wire members (124) and retention eyelets (122) have a thickness of about 0.05 to about 0.3 mm, or about 0.05 to about 0.15 mm.

In other embodiments, the thickness of the outer support frame is constant. As yet another alternative, particularly when the support structure of the implant is cut (e.g., using a laser), stamped or otherwise fabricated from a sheet of material (e.g., titanium or other metal), the outer periphery of the outer support frame can be rounded in order to eliminate sharp edges. This can be accomplished, for example, by tumbling (also known as barreling) the support structure prior to molding (or otherwise forming) the plate about the inner support frame. This process can be applied to any of the support structures (119, 219, 319, 419, 519) described herein.

Figure 12:
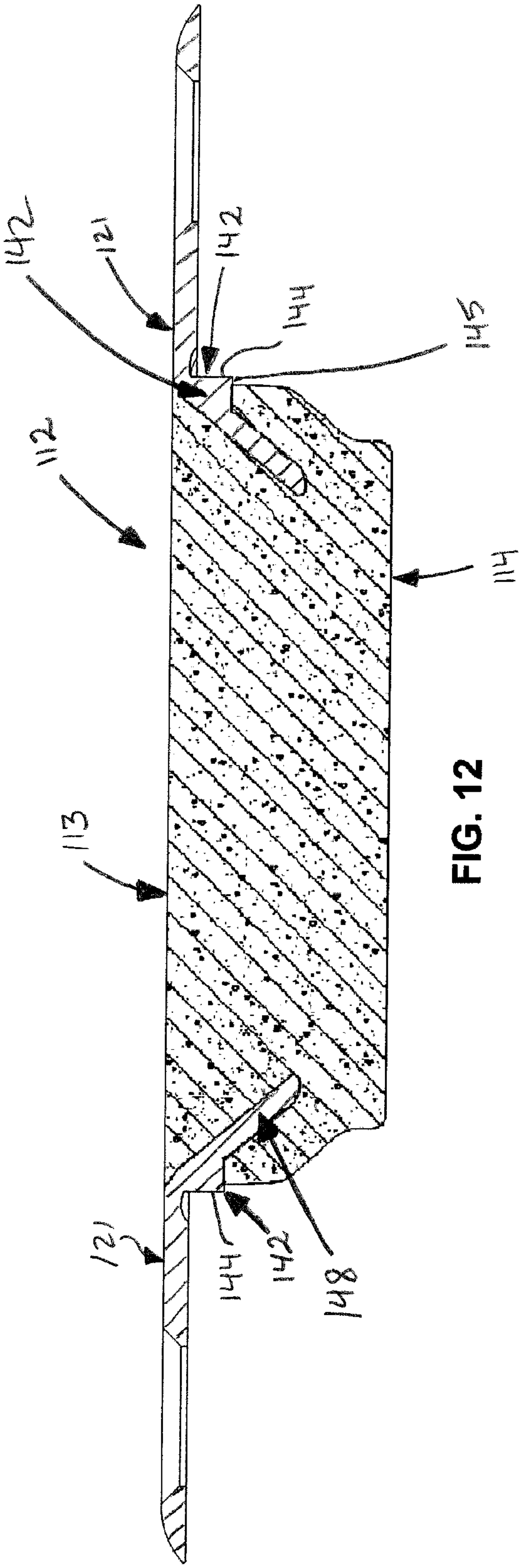
FIG. 12 is a cross-sectional side view similar to that of FIG. 11, wherein the entire implant (including the biocompatible plate) is depicted.
Figure 13:
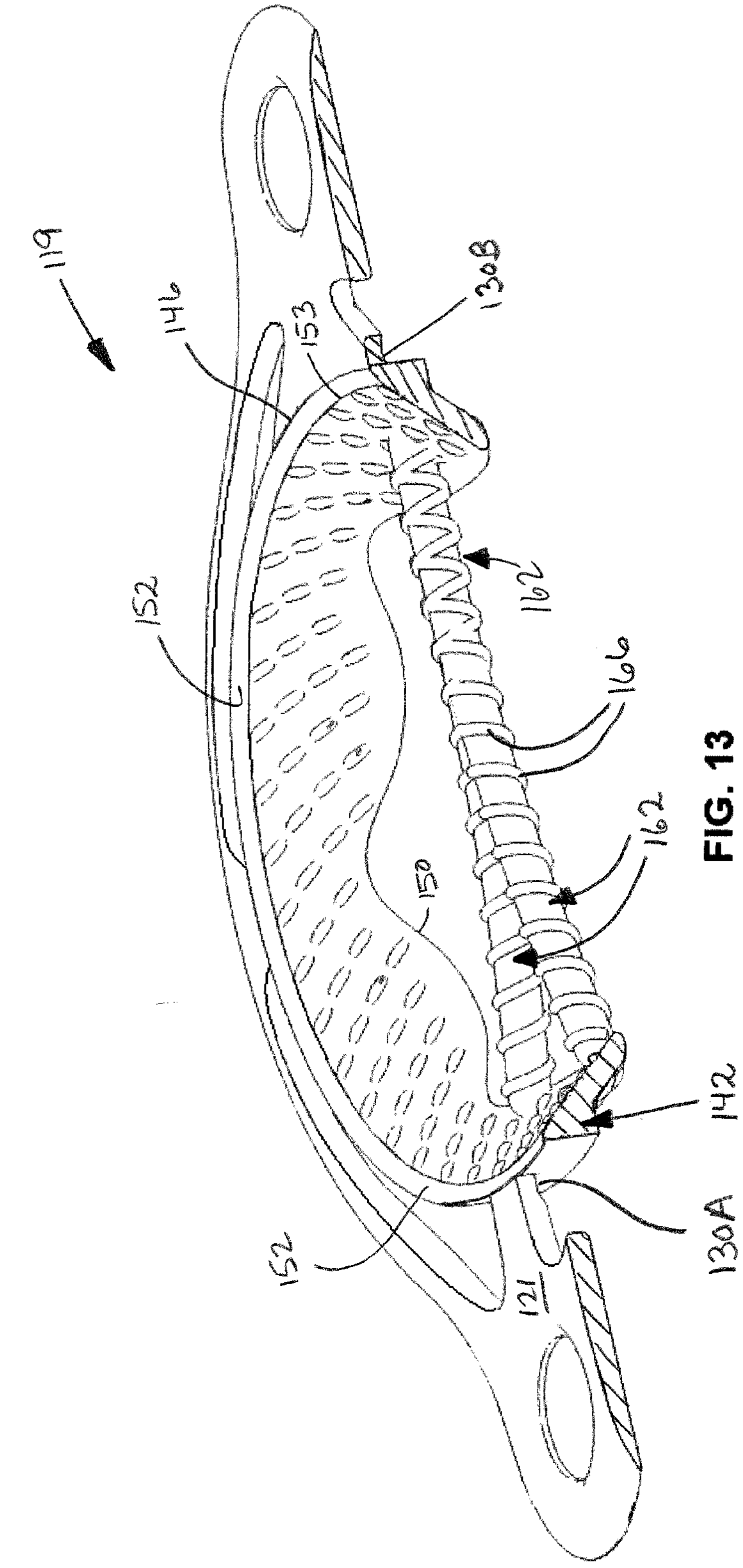
FIG. 13 is a cross-sectional perspective view of the support structure of FIG. 6.

As best seen in the cross-sectional view of FIG. 12, biocompatible plate (112) is supported by the inner support frame (140) such that the inner support frame is partially embedded within the plate (112). In this particular embodiment, the support members (162), the entirety of the sidewall (148), and the majority of annular flange (142) are embedded within the plate (112). Only the outer surface (144) and a small portion of the bottom surface (145) of the flange (142) is exposed (i.e., not located within the plate (112)). In addition, the upper surface (113) of the plate (112) extends over at least a majority of, and, in the embodiment shown, substantially all of, the upper surface (152) of the inner support frame (140). In other embodiments, only support members, the sidewall (148) (or other inner surface of the ring-shaped structure), and optionally a portion of the upper and bottom surfaces of the ring-shaped structure, are covered by the plate material.

The upper surface (113) of the biocompatible plate (112) is flush (or nearly flush) with the upper surface (121) of the outer support frame (120) (see FIGS. 3 and 12), particularly about the upper outer perimeter of the plate (e.g., when the upper surface of the plate is convexly curved, as with implant (400)). The eyelets (122) can also be countersunk, as shown, so that the head of a screw inserted therethrough will not extend above the upper surface (121) of the outer support frame.

While the embodiment of FIGS. 1-16 can be used to fill nearly any bore hole (including those associated with a bone flap, see FIG. 47), it is particularly suited for filing a bore hole that is not associated with a bone flap. In these instances, there is typically solid bone (e.g., the patient's skull) surrounding the entire periphery of the bore hole, and thus two fastening points will be sufficient to secure the implant in place-particularly since the implant can be easily oriented in the bore hole so as to locate the eyelets in a desirable location (e.g., where there is sufficient bone beneath each eyelet).

Other embodiments of the bore hole implants of the present disclosure have more than two fastening points, such as 3, 4, 5, 6, 7 or 8 fastening points (e.g., retention eyelets) arrayed around the plate. In some instances, more than two fastening points may be desired or necessary to provide more fastening point options than merely two located 1800 apart, and/or to allow for the use of more than two fastening points to secure the implant in place. In the case of reattaching a bone flap to surrounding skull, it may be desirable to have at least two fastening points for securing the implant to the bone flap, as well as at least two fastening points for securing the implant to the patient's skull adjacent the bone flap (i.e., at least four fastening points). Also, in some instances the shape, thickness and/or viability of the bone surrounding a bore hole, whether a singular hole or one of several holes used to create a bone flap, may be such that more than two fastening point options are desired or necessary. In these situations, although the bore hole implant is configured to have three or more fastening points, it is not necessary to use all of the fastening points to secure the implant in place. Instead, fewer than all of the fastening points of an implant (e.g., two of four, two of six, four of six, etc.) can be used, with the fastening points selected in order to optimize implant securement based on the shape, thickness and/or viability of the bone.

FIGS. 17-23 depict an alternative embodiment of a bore hole implant (200) having four fastening points (retention eyelets (222)) that is particularly suited for use in reattaching a bone flap (see FIG. 47, wherein two of the implants (200) are depicted being used to reattach a bone flap (B) using screws (203). It should be noted that the reference numerals in FIGS. 17-23 refer to the same (or similar) components of like numerals in the preceding implant embodiment (e.g., eyelets (222), plate (212), etc.).

Like the previously described embodiment, implant (200) generally comprises a biocompatible plate (212) and a support structure (219) comprising an outer support frame (220) and an inner support frame (240). The plate (212) and inner support frame (240) are configured identical to plate (112) and inner support frame (140) of the previously described embodiment. As in the previous embodiment, only outer surface (244) and a small portion of the bottom surface of the flange (242) is exposed (i.e., not embedded within the plate (212)).

Figure 22:
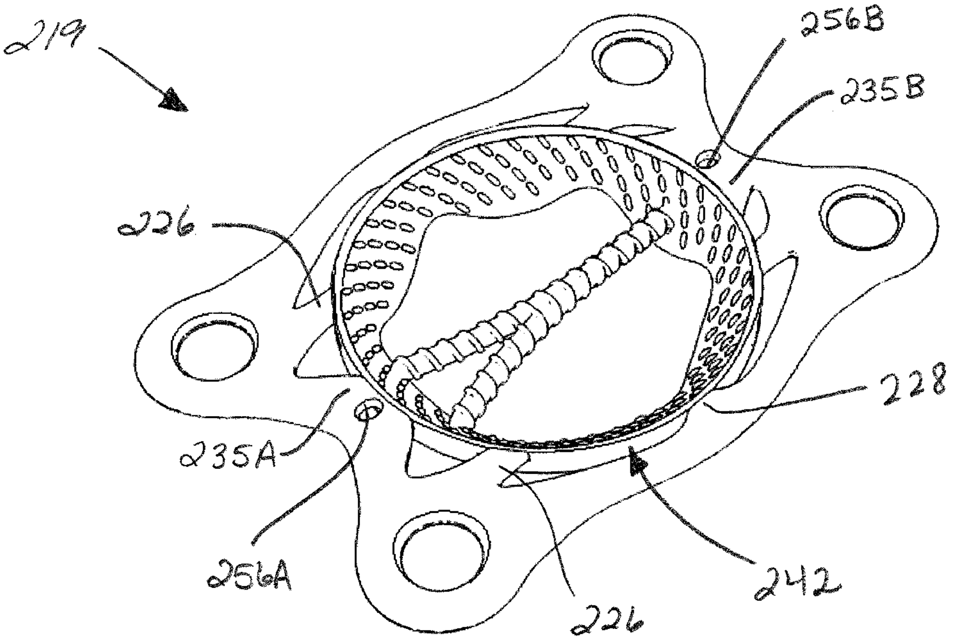
FIGS. 22 and 23 depict a perspective view and top plan view, respectively, of the support structure of the implant of FIG. 17.
Figure 23:
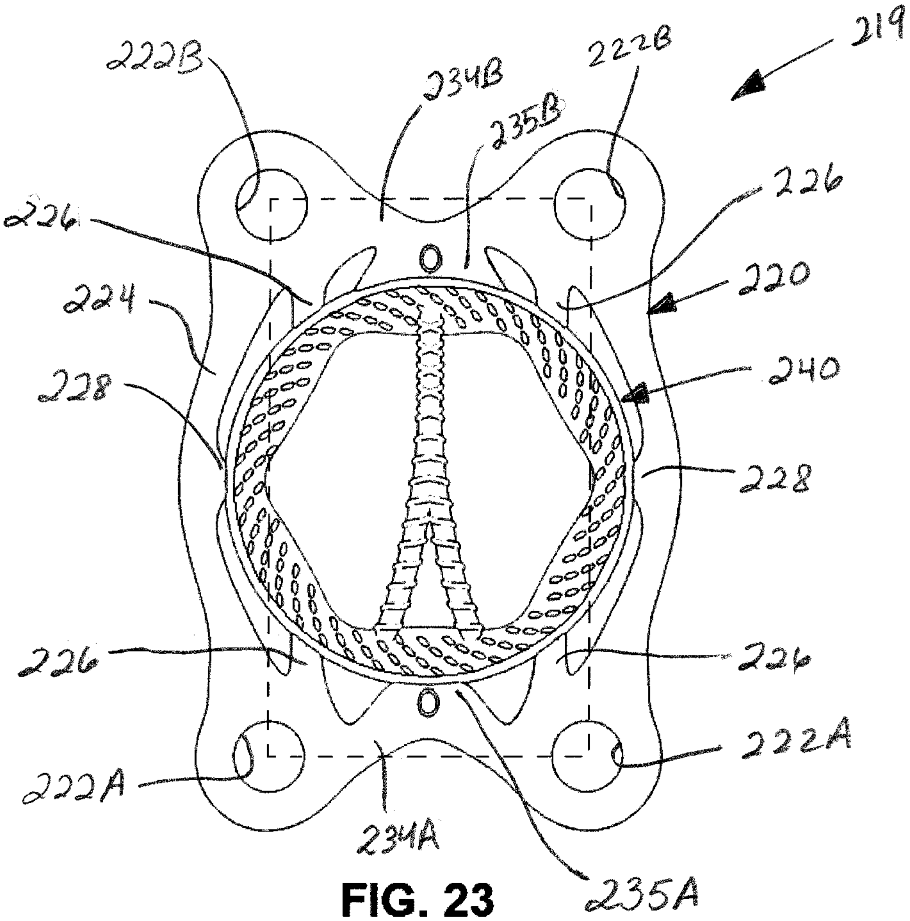

FIGS. 22 and 23 depict the support structure (219) in more detail, with the plate (212) omitted for clarity. As before, support structure (219) comprises an outer support frame (220) that is connected to and spaced away from an inner support frame (240). Outer support frame (220) comprises a plurality of fastening points—in this instance four fastening points in the form of retention eyelets (222). The retention eyelets (222) are adapted to receive a fastener therethrough, such as a bone screw, suture or other fastener known to those skilled in the art, for attaching the implant to bone surrounding a bore hole. Retention eyelets (222) are arranged about the periphery of the implant (200) in a rectangular arrangement, as shown in FIG. 23. Thus, a first pair of retention eyelets (222A) is located along one edge of the implant (200), and a second pair of retention eyelets (222B) is located along the opposite edge of the implant. When implant (200) is used to reattach a bone flap, bone screws inserted through one pair of retention eyelets are used to secure the implant (200) to the bone flap and bone screws inserted through the other pair of retention eyelets are used to secure the implant (200) to the skull adjacent the site of reattachment, with the biocompatible plate (212) located within a bore hole that extends between the bone flap and the skull adjacent the bone flap opening. It will be understood, however, that in some instances less than all of the retention eyelets are used for fastening implant (200) in place, particularly when the implant (200) is used to fill a single bore hole rather than for reattaching a bone flap.

The retention eyelets (222) can be arranged in a variety of other configurations besides the rectangular arrangement shown. For example, the eyelets can be arranged in trapezoidal arrangement such that the distance between the second pair of eyelets (222B) is greater than the distance between the first pair of eyelets (222A). In addition, although the first and second pairs of eyelets (222A, 222B) are depicted as being spaced the same distance from the biocompatible plate (212), alternative arrangements may be employed wherein one pair of eyelets is spaced further from the plate than the other pair (i.e., so that the center of the imaginary rectangle shown in dashed line in FIG. 23 does not coincide with the center of the plate (212)). The eyelets can also be arranged in a square arrangement (i.e., located around the plate (212) equidistant from adjacent eyelets). Less than or more than four eyelets (222) can also be provided, such as three, five, six, seven or even eight retention eyelets arranged about the plate in a variety of patterns.

As in the previous embodiment, the outer support frame (220) includes a first pair of convexly curved wire members (224), each of which extends between a retention eyelet (222A) and a retention eyelet (222B) such that the wire members (224) extend along opposite sides of the implant (200). A second pair of concavely shaped wire members (234A, 234B) is also provided. Wire member (234A) extends between the first pair of retention eyelets (222A), and wire member (234B) extends between the second pair of retention eyelets (222B). Thus, the wire members (224, 234A, 234B) and the eyelets (222) encircle, and are spaced away from, the outer surface (244) of the inner support frame.

Once again, the outer support frame (220) is connected to the inner support frame (240) by a plurality of struts. End struts (235A, 235B) extend between and connect wire members (234A, 234B) and outer surface (244) of the inner support frame, and are essentially extensions of the wire members (234A, 234B) that connect with the outer surface (244) of the inner support frame. The outer support frame (220) is further connected to the inner support frame (240) by eyelet struts (226), each of which extends between and connects a retention eyelet (222A, 222B) and outer surface (244) of the inner support frame. Thus, four such eyelet struts (226) are provided. Along both sides of the implant, intermediate a retention eyelet (222A) and a retention eyelet (222B), a side strut (228) extends between and connects each wire member (224) and outer surface (244) of the inner support frame (240). As with the previous embodiment, end strut (235B) is wider than end strut (235A) and increases in width towards flange (242) in order to provide additional support during fabrication, particularly when the support structure (119) is fabricated by SLM and similar additive manufacturing techniques. In particular, the configuration of the end struts (235A, 235B) allows the support structure (219) to be self-supporting during SLM fabrication.

As in the previous embodiment, the struts (226, 228, 235A, 235B) are thinner than the height of the outer surface (244), and connect to the outer surface (244) such that the upper surfaces of the struts are generally flush (or nearly flush) with the upper edge of the inner support frame. Of course, any number of struts extending between and connecting the outer frame to the outer surface (244) of the inner frame can be provided. For example, in alternative embodiments the eyelet struts (226) are omitted such that the outer support frame is more easily deformed for purposes of adjustment prior to implantation. Thus, the number, shape and location of the connecting struts may be varied, as desired.

Because the outer support frame is connected to the internal support frame external to the plate (212) (i.e., at outer surface (244)), the wire members and struts can be deformed (i.e., bent) without risk of cracking the plate (212). Like the previous embodiment, deformation zones are provided on portions of the struts (226, 228, 235A, 235B) adjacent to the outer surface (244) of the flange (240) in order to facilitate deformation of the outer support frame. In specific embodiments, similar to the previously described embodiment, each strut (226, 228, 235A, 235B) includes a deformation zone comprising a reduced-thickness region in the form of a notch extending upwardly from the bottom surface of the strut, and located immediately adjacent the outer surface (244) of the inner support frame (see FIGS. 20 and 21). Accordingly, the struts (226, 228, 235A, 235B) are thinnest where they meet the cylindrical outer surface (244). Once again, in specific embodiments, the reduced-thickness regions span the entire width of their respective struts, and are generally curved so as to match the curvature of the cylindrical outer surface (244). Apertures (256A, 256B) are provided in the end struts (235A, 235B) (see FIG. 22) in order to increase the flexibility of the end struts and to reduce the amount of material used in support structure (219).

As discussed previously, in addition to or in place of the reduced-thickness regions on the struts (226, 228, 235A, 235B), deformation zones in the form of pleated regions may also be provided on any of the struts and/or the wire members (224, 234A, 234B). Also, it will be understood that the implant (200) may be modified such that deformation zones are not provided on all of the struts (226, 228, 235A, 235B). As yet another alternative, reduced-thickness regions may be configured to comprise a notch or other recess that extends downwardly from the upper surface of the strut, instead of or in addition to one that extends upwardly from the bottom surface of the strut. Furthermore, deformation zones comprising reduced-width regions may be provided on the struts, instead of or in addition to the reduced-thickness regions.

Figure 19:
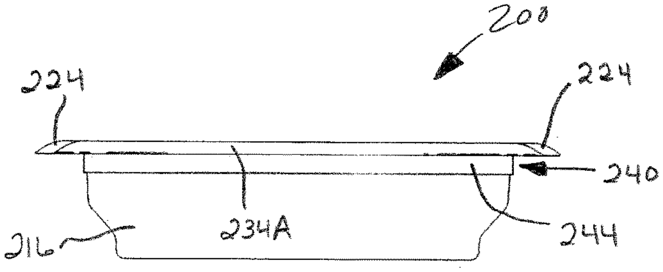
Figure 20:
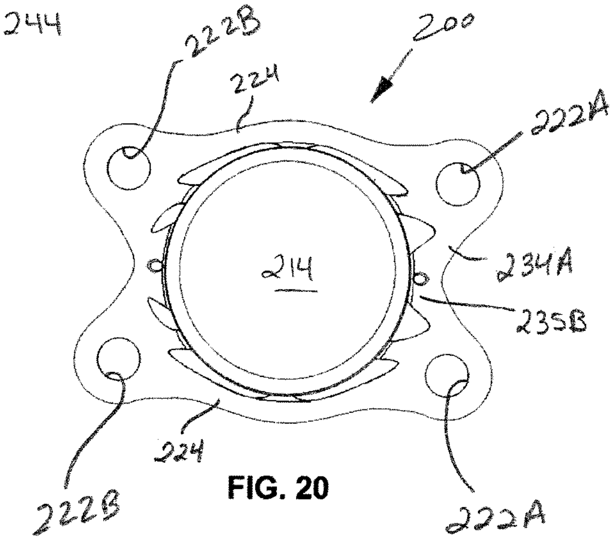
Figure 21:
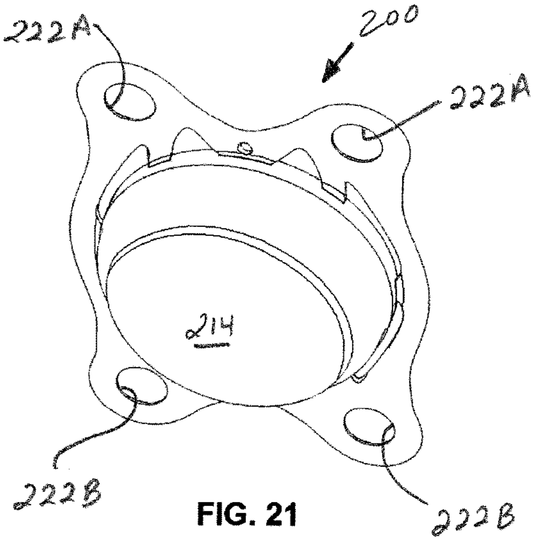

The outer periphery of the outer support frame (220) is also tapered as shown in FIG. 19. This tapering around the periphery of the outer support frame improves implant fit and aesthetics by providing a smooth, reduced height transition between the surface of surrounding bone and the upper surface of the implant. By way of example, the outer support frame has a thickness of about 0.2 to about 0.6 mm, or about 0.3 to about 0.45 mm, and the outer edges of the wire members (224) and retention eyelets (222) have a thickness of about 0.05 to about 0.3 mm, or about 0.05 to about 0.15 mm.

Figure 24:
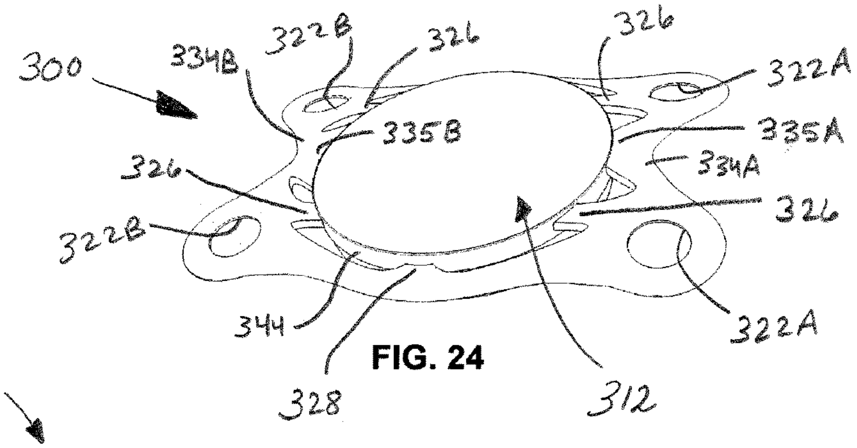
FIG. 24 is a perspective view of yet another embodiment of a bore hole implant.
Figure 25A:
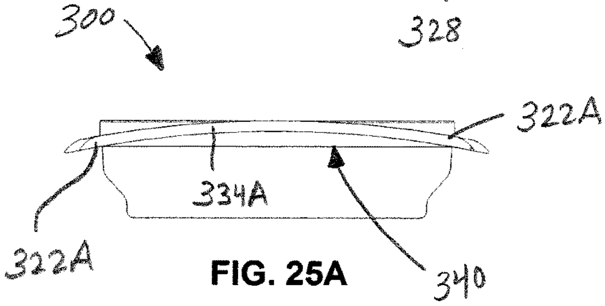
FIG. 25A depicts a side view of the implant of FIG. 24.
Figure 25B:
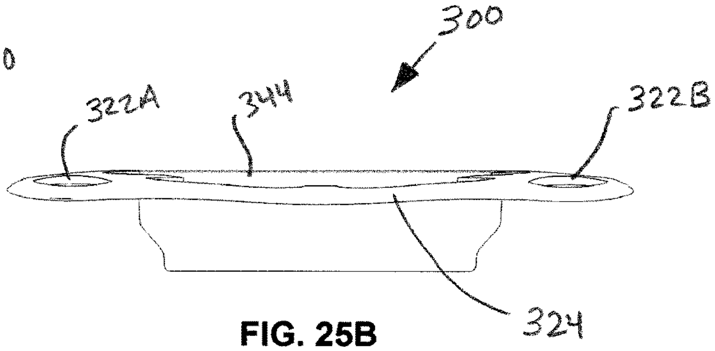
FIG. 25B depicts a side view of the implant of FIG. 25A, rotated 90 degrees from the view of FIG. 25A.
Figure 26:
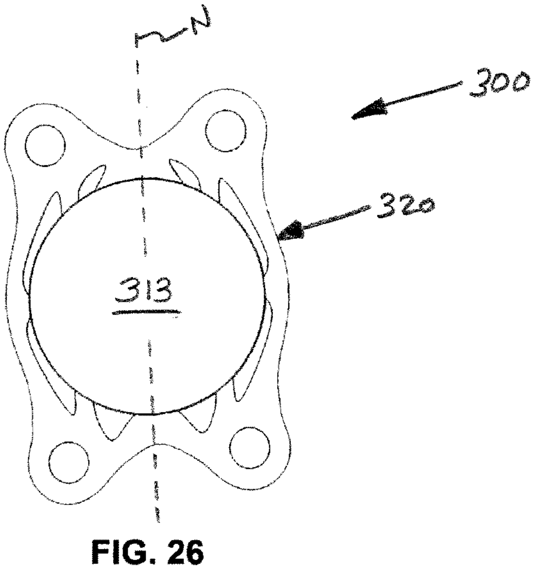
FIG. 26 depicts a top plan view of the implant of FIG. 24.
Figure 27:
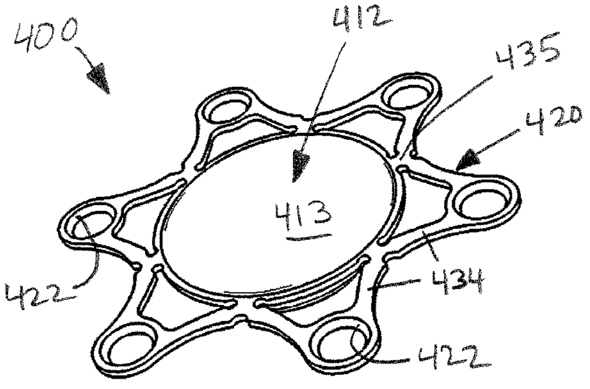
FIG. 27 depicts a perspective view of a further embodiment of a bore hole implant.
Figure 28:
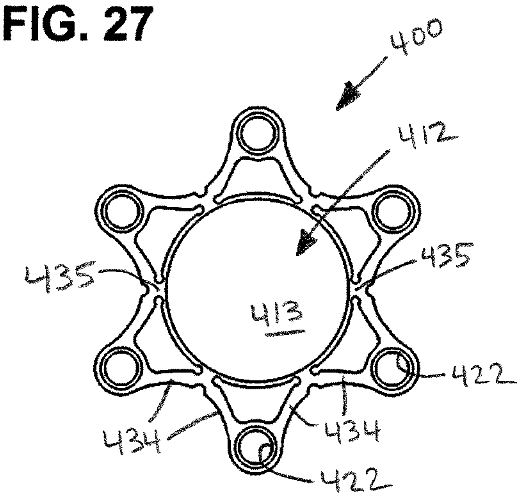
FIG. 28 depicts a top plan view of the implant of FIG. 27.

FIGS. 24-26 depict yet another embodiment of a bore hole implant (300). Implant (300) is nearly identical in construction to implant (200), and thus generally comprises a biocompatible plate (312) and a support structure comprising an outer support frame (320) having four fastening points (retention eyelets (322)), and an inner support frame (340). The plate (312) and inner support frame are configured identical to the plate (112, 212) and inner support frame (140, 240) of the previously described embodiments. As in the previous embodiments, only outer surface (344) and a small portion of the bottom surface of the flange (340) of the inner support frame are exposed (i.e., not embedded within the plate (312)). Once again, the reference numerals in FIGS. 14-26 refer to the same components of like numerals in the preceding implant embodiments (e.g., eyelets (322), plate (312), etc.).

While the outer support frames of the previously described embodiments were, as fabricated, substantially coplanar with the upper surface (113, 213) of the biocompatible plate (112, 212) such that the upper surface of the plate is flush (or nearly flush) with the upper surface of the outer support frame, the outer support frame (320) of implant (300) is curved about at least one axis. In the particular embodiment shown, the outer support frame is curved about an axis (N) (see FIG. 26) that extends across the top surface of the implant through the centers of wire members (334A, 334B) and their respective end struts (335A, 335B). Thus, although the struts (326, 328, 335A, 335B) are once again thinner than the height of the outer surface (344) and the upper surfaces of end struts (335A, 335B) are generally flush with the upper edge of the outer surface (344), the eyelet struts (326) and side struts (328) are located progressively lower on outer surface (344). In particular, the bottom surface of side struts (328) is approximately flush with the lower edge of outer surface (344), and eyelet struts (326) are positioned intermediate the upper and lower edges of the outer surface (344). As a result, the wire members (334A, 334B) and eyelets (322A, 322B) are curved, with their bottom surfaces (i.e., the surface which will rest against the patient's skull following implantation) concavely curved so as to approximate the curvature of regions of a typical skull (see FIG. 25A). The wire members (324) extending along either side of the implant (300) are also curved, but to a lesser extent since they extend generally along the axis (N) of curvature. Alternatively, the outer support frame can be curved about an axis that extends orthogonal to axis (N), such that the upper surfaces of the side struts (328) are flush with the upper edge of the outer surface (344). As a further alternative, the outer support frame can be configured to have any of a variety of simple or complex curvatures, such as being curved about more than one axis. If desired, deformation zones similar to those described previously can also be provided on the struts (326, 328, 335A, 335B), as well as on other portions of the outer support frame.

By fabricating the implant so that the outer support frame is curved, the outer support frame can more closely approximate the curvature of the patient's skull, thereby reducing the amount of adjustment (i.e., deformation) that might otherwise be necessary if the outer support frame is substantially planar.

FIGS. 27-36 depict yet another alternative embodiment of a bore hole implant (400), in this instance having six fastening points (retention eyelets (422)), that is particularly useful for reattaching a bone flap (see FIG. 47, wherein an implant (400) is depicted being used to reattach a bone flap (B) using a pair of screws (203) and two of the six eyelets). It should be noted that the reference numerals in FIGS. 27-36 refer to the same (or similar) components of like numerals in the preceding implant embodiment (e.g., eyelets (422), plate (412), etc.). Also, any number of retention eyelets can be provided on this embodiment, such as two, three, four, five, six, seven or even eight retention eyelets, arranged about the inner support frame and plate in a variety of patterns.

Like the previously described embodiment, implant (400) generally comprises a biocompatible plate (412) and a support structure (419) comprising an outer support frame (420) connected to, and spaced away from, an inner support frame (440). The plate (412) is configured similar to the plates (112, 212) of the previous embodiments, but has a slightly different shape. Plate (412) has an upper surface (413), a bottom surface (414), a central axis (L'), and a sidewall (416) comprising a surface of revolution about the central axis (L'), and therefore has a circular cross-section through any plane perpendicular to its central axis (L'). The diameter of the plate (412) tapers such that its diameter is smallest adjacent the bottom surface (414) and is largest adjacent the top surface (413). Plate (412) includes a tapered upper cylindrical section (417A), a tapered lower cylindrical section (417B), and a curved transition segment (417C) extending therebetween (see FIG. 29B). The upper and lower sections (417A, 417B) also taper curvilinearly, as shown, with the lower edge (418) of the lower section (417B) radiused where it meets the bottom surface (414) in order to avoid a sharp edge. The tapered nature of the upper cylindrical section (417A) facilitates removing the plate (412) from its mold as well as the insertion of the plate (412) into a bore hole.

The inner support frame (440) of the support structure (419) can be configured similar or identical to the inner support frames (140, 240) described above. Alternatively, in the embodiment of FIGS. 27-36 the inner support frame (440) comprises a flat, annular ring (442) having an outer surface (444), an inner surface (451), an annular upper surface (452), and an annular bottom surface (445). In the embodiment shown, outer and inner surfaces (444, 451) are surfaces of revolution, in this specific instance cylindrical surfaces. While the outer and inner surfaces (444, 451) are depicted as being right cylindrical surfaces (i.e., non-tapered), it will be understood that one or both of these surfaces can be tapered cylinder surfaces e.g., the outer diameter of surfaces (444, 451) can taper slightly through their heights (e.g., a frustoconical surface when the taper is constant). The inner support frame (440) is configured such that no portion will be positioned within the bore hole during implantation. Instead, the inner support frame remains outside of the bore hole, located against the surface of the bone surrounding the bore hole.

The annular ring (442) (i.e., the outer surface (444) thereof) has an outer diameter slightly larger than the outer diameter of the upper end of the plate (i.e., the diameter of the upper surface (413) and/or the outer diameter of the plate where it meets the bottom surface (445) of the inner support frame). In one embodiment, the annular ring (442) has an outer diameter between about 0.03 and about 0.15 cm larger than the outer diameter of the upper end of the plate (412). In one particular embodiment, the annular ring (442) has an outer diameter between about 0.07 and about 0.09 cm larger than the outer diameter of the plate (412). The width of the annular ring (442) (i.e., the difference between the outer and inner diameters of the ring) defines how much of the ring (442) will be embedded within the plate (412). The width of the annular ring is also chosen to ensure that the small gap between the outer diameter of the plate and the diameter of the bore hole is covered by the annular ring (442), not only for aesthetics but also to help prevent fibrous tissue ingrowth between the plate and the inner wall of the bore hole which may prevent bone growth in the gap between the plate and the inner wall of the bore hole.

In the depicted embodiment, the outer diameter of the upper end of the plate (412) is at least as large as the inner diameter (i.e., inner surface (451)) of the annular ring (442) so that the entirety of the inner surface (451) of the annular ring (442) is covered by the plate material. There is no gap between the inner surface (451) and the plate (412).

Particularly when the implant is formed by molding the plate onto the inner support frame, it may be difficult to ensure that the plate is molded in the precise dimensions necessary to prevent a gap between the ring and the outer surface of the plate (412). Thus, as best seen in FIGS. 36A and 36B, portions of the upper surface (452) and bottom surface (445) of the annular ring (442) are covered by the plate material. When deformation zones (e.g., notches 430A, 430B described below) are provided on the annular ring (442), the plate material generally should not cover the deformation zones in order to avoid cracking of the plate material. In one embodiment, the width of the annular ring (442) is such that less than 75%, less than 65%, less than 50%, or less than 30% of the width of the annular upper surface (452) of the annular ring (442) is covered by the plate material. In the particular embodiment shown, about 50% of the width of the ring (442) is covered by the plate (412) material (see FIGS. 36A and 36B). It will be understood, however, that when the plate is molded onto the inner support frame, the amount of plate material extending over the upper surface (452) can vary. In general, the amount of plate material covering the bottom surface (445) of the annular ring is less than the amount covering the upper surface (452) (e.g., less than 65%, less than 50%, or less than 20% of the width of the annular bottom surface (445)).

The outer support frame (420) is connected to and spaced away from the inner support frame (440), and includes a plurality of fastening points adapted for attaching the implant to bone. In this instance, six fastening points in the form of retention eyelets (422) are provided. The retention eyelets (422) are adapted to receive a fastener therethrough, such as a bone screw, suture or other fastener known to those skilled in the art, and may be countersunk as shown. The eyelets (422) are evenly arrayed about the periphery of the implant in a hexagonal arrangement. Thus, imaginary lines extending between adjacent eyelets (422) form a hexagon, with the eyelets located at the vertices thereof (see FIG. 30). When implant (400) is used to reattach a bone flap, bone screws are inserted through two or more (e.g., all six or less than six) of the retention eyelets in order to secure the implant (400) to bone. As previously noted, the retention eyelets (422) can be arranged in a variety of other configurations besides the hexagonal arrangement shown in FIG. 30. In addition, although the eyelets (422) are depicted as being spaced the same distance from the biocompatible plate (412), alternative arrangements may be employed wherein one or more eyelets are spaced further from the plate than the others.

Figure 33:
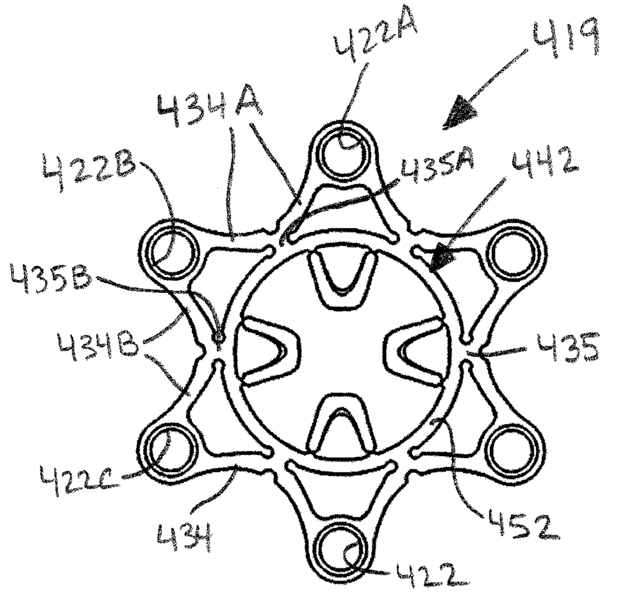
FIG. 33 depicts a top plan view of the support structure of FIG. 32.

Each eyelet (422) is connected to each of the two adjacent eyelets by wire members (434) that extend therebetween. Each wire member (434) is connected to the annular ring (442) by one or more struts (435). In some embodiments the wire members (434) extend along a straight line between adjacent eyelets (422). In the embodiment shown, however, the wire members (434) are concavely curved—in this instance, concavely curved about an axis parallel to the central axis of the plate (so that the support structure (419) can be formed from a sheet of material). The strut (435) connecting the wire member (434) to the annular ring extends radially inward from approximately the midpoint of the wire member. Thus, as shown in FIG. 33, a first wire member (434A) extends between the first and second eyelets (422A, 422B), and is connected to the annular ring (442) (at the midpoint of the wire member) by a first strut (435A). Similarly, a second wire member (434B) connects second and third eyelets (422B, 422C), and the second wire member (434B) is connected to the annular ring (442) by a second strut (435B). Thus, together the wire members (434) and the eyelets (422) encircle the annular ring (442) of the inner support frame.

Because the outer support frame is connected to the internal support frame external to the plate (412) (i.e., at outer surface (444) of the annular ring (442)), the wire members (434) and struts (435) can be deformed (i.e., bent)

without risk of cracking the plate (212). Deformation zones can once again be provided to facilitate deformation in order to orient the retention eyelets and wire members to better match the curvature of surrounding bone. Any of the previously described types of deformation zones can be employed, including regions of reduced cross-section (width and/or thickness) as well as pleated regions.

Figure 33A:
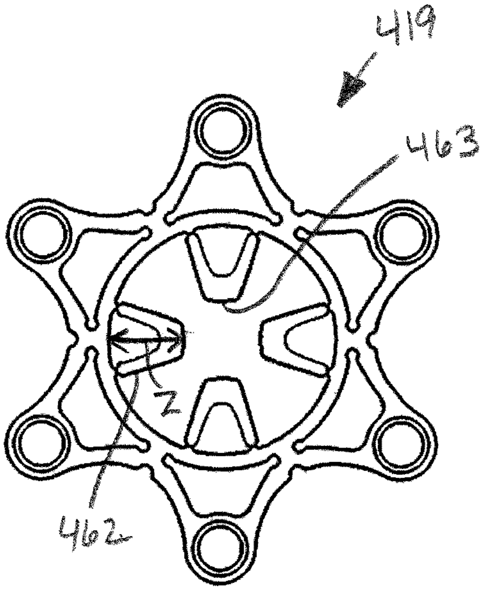
FIG. 33A depicts a top plan view of the support structure of FIG. 32, prior to the support members being bent downwardly.
Figure 33B:
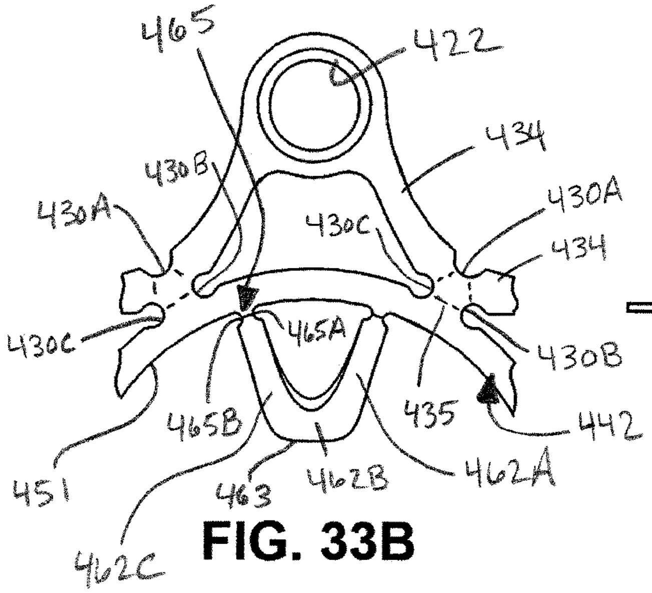
FIG. 33B is an enlarged view of a portion of FIG. 33.
Figure 34:
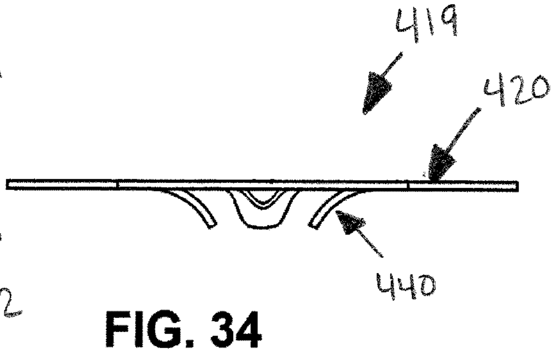
FIG. 34 depicts a side plan view of the support structure of FIG. 32.

In the depicted embodiment, as best seen in FIG. 33B, a first arcuate notch (430A) is provided in the wire member (434), with the notch extending radially inward from the outer surface of the wire member (434) towards the center of the support structure. A second arcuate notch (430B) extends into the wire member (434), one side of the adjacent strut (435), and a portion of the annular ring (442) adjacent to the strut (435). A third arcuate notch (430C) extends into the wire member (434), the opposite side of the adjacent strut (435), and a portion of the annular ring (442) adjacent to the opposite side of the strut (435). As a result three deformation zones in the form of reduced-width regions are provided (as indicated by the dashed lines in FIG. 33A): one extending between the first notch (430A) and the second notch (430B); one extending between the first notch (430A) and the third notch (430C); and one extending between the second notch (430B) and the third notch (430C). Three such deformation zones are similarly provided on the other wire members (434) and struts (435), thereby allowing for deformation of the support structure where the outer support frame (420) is attached to the inner support frame (440). The deformation zones provided by the notches allow the outer support frame to be adjusted by bending prior to implantation as well as deform as the implant is attached to bone so that the bottom surfaces of the retention eyelets and wire members lie as flat as possible against the bone.

The inner support frame (440) of the implant (400) also includes an interior support structure embedded within the plate. The inner support frame (440) can include one or more support members similar to those employed in the previously described implants (100, 200, 300) (i.e., similar to support members (162)) that extend inwardly across the interior of the inner annular ring (442), between portions of the inner surface (451) thereof. In the embodiment shown, however, one or more support members (462) extend inwardly from the inner surface (451) of the annular ring (442). At least a portion of each of the support members (462) extends inwardly from the inner surface of the ring-shaped member at an angle with respect to a plane that is orthogonal to the central axis of the plate such that the depth of the support member (462) within the plate varies along its length. In the particular embodiment shown, the support members extend inwardly and downwardly from the inner surface of the annular ring such that the support members are curved along at least a portion of their lengths. The support members (462) provide reinforcement of the plate in order to ensure mechanical stability, while still allowing the plate to be molded over and about the inner support frame.

In the depicted embodiment, four support members (462) are arrayed around the interior of the annular ring (442). As best seen in FIG. 33B, each support member (462) is in the form of a wire loop comprising a first leg (462A) that extends inwardly and downwardly away from a first portion of the inner surface (451) of the annular ring (442), a second leg (462C) that extends inwardly and downwardly away from a second portion of the inner surface (451), and a downwardly angled inner segment (462B) that connects the interior ends of the first and second legs (462A, 462C). The intersections of the first and second legs (462A, 462C) with the inner surface (451) are spaced apart. In the embodiment shown, the first and second legs (462A, 462C) of the support members (462) extend radially inward toward the central axis of the annular ring (442), and also increase in width towards the center of the annular ring (442). Also, the width of the inner segment (462B) is greater than the width of the first and second legs (462A, 462C). Thus, each of the support members (462) generally has a U-shaped configuration when viewed from above (e.g., FIG. 33).

Each of the support members (462) extends inwardly from the inner surface (451) of the annular ring (442) a distance that is less than half the maximum diameter of the plate (412) such that their inner segments (462B) are spaced apart from each other within the plate. Thus, the support members (462) do not contact or overlap one another inside of the plate (although alternative configurations allow for the support members to be bent to different extents such that the support members overlap near the center of the plate). In some embodiments the length (Z) of each support member (462) prior to being bent downwardly (see FIG. 33A) is between about 20% and about 45% of the inner diameter of the annular ring (442). In other embodiments, the length (Z) is between about 30% and about 35% of the inner diameter of the annular ring (442).

Figure 29:
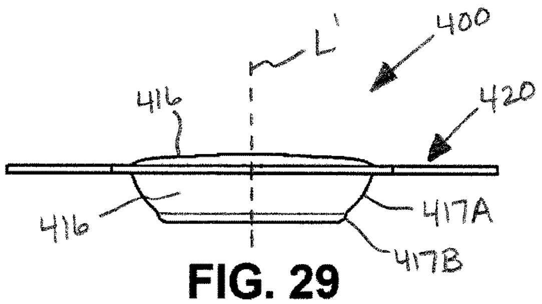
FIG. 29 depicts a side view of the implant of FIG. 27.
Figure 29A:
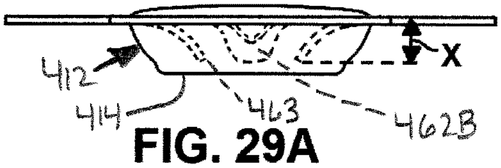
FIG. 29A is the same view as FIG. 29, wherein the portions of the support frame located within the plate are shown in broken line.
Figure 29B:
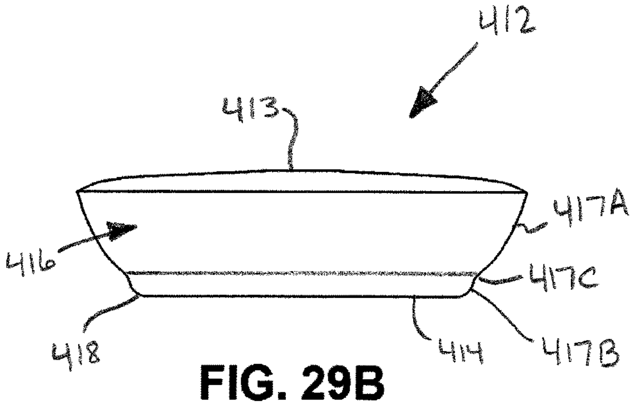
FIG. 29B depicts a side view of the plate of the implant of FIG. 27, with the support structure omitted in order to better depict the configuration of the plate.
Figure 28A:
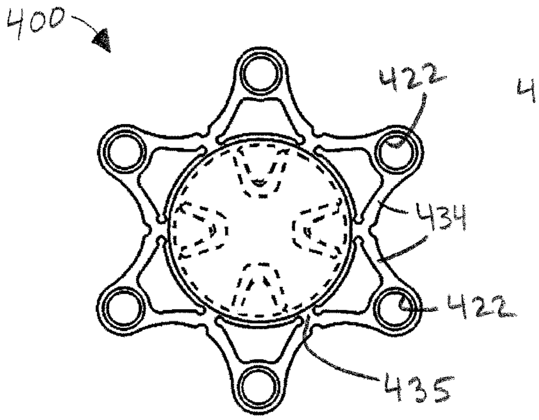
FIG. 28A is the same view as FIG. 28, wherein the portions of the support frame located within the plate are shown in broken line.
Figure 30:
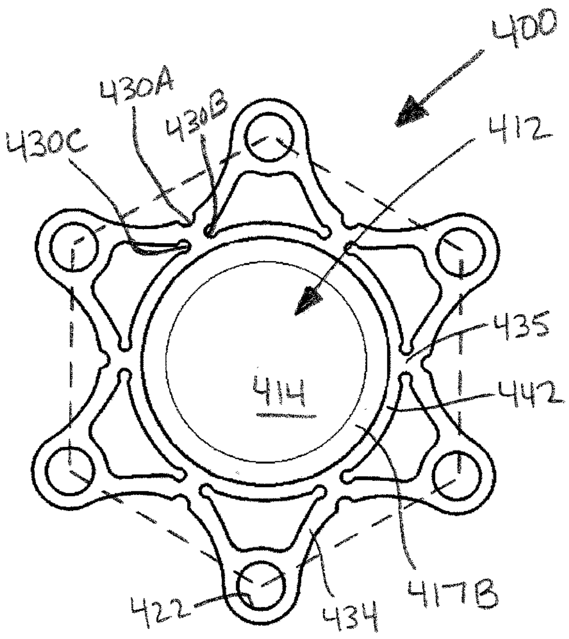
FIGS. 30 and 31 depict a bottom plan view and bottom perspective view, respectively, of the implant of FIG. 27.
Figure 31:
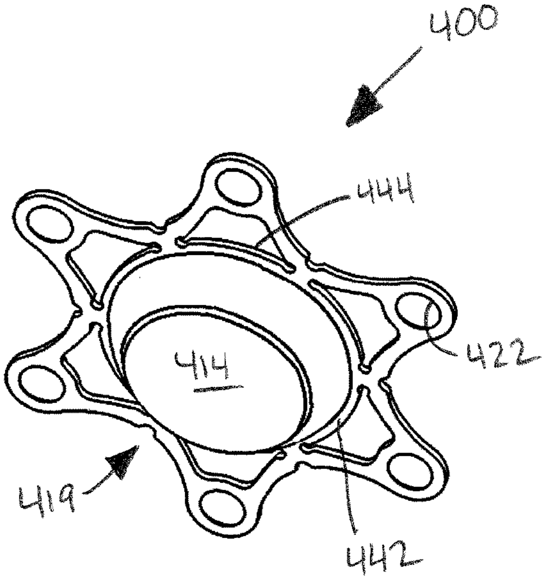

The support members (462) also curve downwardly, as shown, such that the lower-most edge (463) of each support member (i.e., the interior edge of the inner segment (462B)) is spaced away from the bottom surface (414) of the plate (412) by a distance that is less than 50% of the maximum thickness of the plate (412) (see FIG. 29A). In other embodiments, the lower-most edge (463) is spaced away from the bottom surface (414) of the plate (412) by a distance that is less than 40%, less than 30% or less than 20% of the thickness of the plate (412). Accordingly, the depth (X) of the inner support frame (440), as measured from the upper surface (452) of the annular ring (442) to the lower-most edge (463) of each support member (462) (see FIG. 29A) is more than 50%, more than 60%, or more than 65% of the maximum thickness of the plate (412). It will be understood, however, that any number and arrangement of support members that partially extend into the interior of the inner support frame (440) may be provided.

The support members (462) can optionally be textured, thereby providing an uneven surface that not only improves cement adherence to the support members (462), but also helps prevent fracturing of the cement along a fracture surface extending along the support members (462). Such texturing can be in the form of a plurality of protrusions and/or depressions in the surfaces, such as the spiral ridges described previously, or even a roughened (i.e., not smooth) surface.

Figure 32:
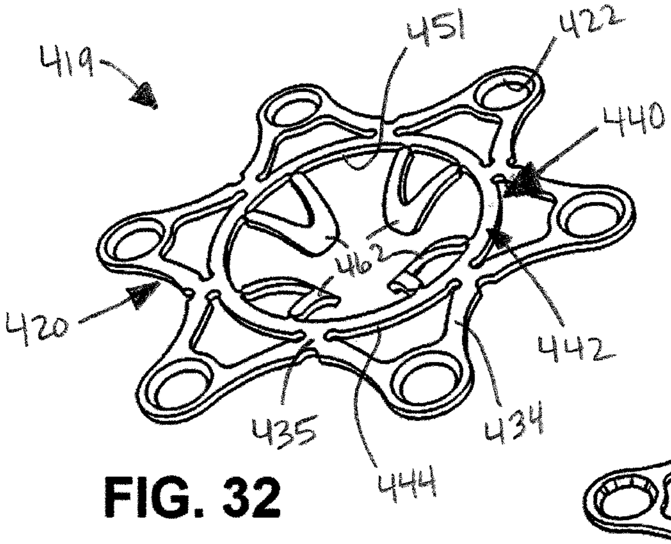
FIG. 32 depicts a perspective view of the support structure of the FIG. 27 implant.
Figure 32A:
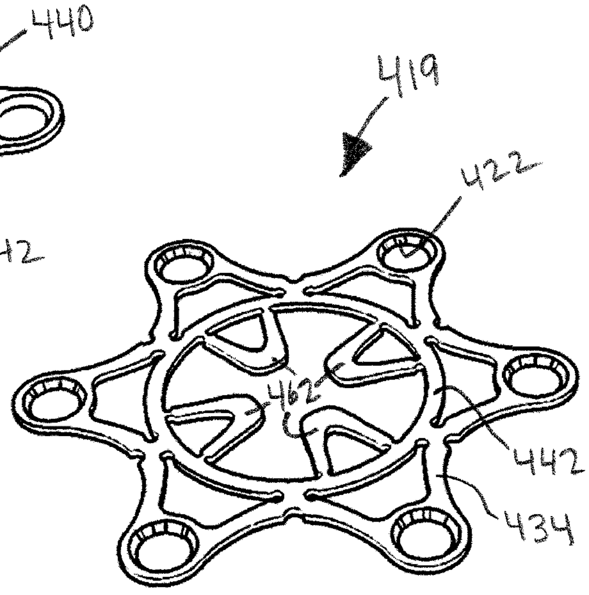
FIG. 32A depicts a perspective view of the support structure of FIG. 32, prior to the support members being bent downwardly.

FIGS. 32A and 33A depict the support structure (419) as manufactured from a flat sheet of material (e.g., titanium). The support members (462) are initially flat, in the same plane as the entirety of the support structure. After the support structure has been cut or stamped from a sheet of material (or formed in another manner), each of the support members (462) is bent downwardly into the orientation shown in FIGS. 32 and 34. The support members can be bent by hand or using any of a variety of tools and/or jigs (to ensure that the support members are properly bent to the desired orientation). In order to facilitate bending of the support members (462), deformation zones (465) can be provided where the first and second legs (462A, 462C) of the support members intersect the inner surface (451) of the annular ring (442). In the embodiment shown, the deformation zones comprise arcuate notches (465A, 465B) provided on opposite sides of the outer terminal ends of the first and second legs (462A, 462C) of the support members (462), thus creating a reduced-width region where the first and second legs (462A, 462C) intersect the inner surface (451). Of course, any of the other types of deformation zones described herein can be employed instead, or in addition to, the arcuate notches (465A, 465B).

FIGS. 37-46 depict another alternative embodiment of a bore hole implant (500) having two fastening points (retention eyelets (522)). It should be noted that the reference numerals in FIGS. 37-46 refer to the same (or similar) components of like numerals in the preceding implant embodiment (e.g., eyelets (522), plate (512), etc.).

The plate (512) and inner support frame (540) of the embodiment of FIGS. 37-46 are identical to the plate (412) and inner support frame (440) of the previously described implant (400). Thus, the inner support frame (540) of the support structure (519) includes an annular ring (542) and four inwardly and downwardly extending internal support members (562), configured in the same manner as support members (462) described above (including bending the support members (562) downwardly in the manner described above with respect to implant (400) following fabrication of the support structure 519).

In this embodiment, however, the outer support frame (520) comprises a pair of fastening points in the form of retention eyelets (522) adapted to receive a fastener therethrough. The retention eyelets (522) are located at opposite ends of the implant (500) such that an imaginary line intersecting the centers of retention eyelets (522) also intersects the central axis of the plate. Each eyelet (522) of the outer support frame (520) is connected to the outer surface (544) of the annular ring (542) by a pair of wire members (534) that extend therebetween. The wire members (534) connecting each eyelet to the annular ring diverge away from each other such that the distance between the wire members (534) adjacent the annular ring (542) is greater than the distance between the wire members (534) adjacent the eyelet (522). While the wire members (534) can extend along a straight line between adjacent the eyelet (522) and the annular ring, in the embodiment shown the wire members (534) are slightly concavely curved. It will also be understood that this same arrangement (a pair of wire members connecting each eyelet to the annular ring) can be employed with more than two eyelets (e.g., three, four or five eyelets).

Figure 42:
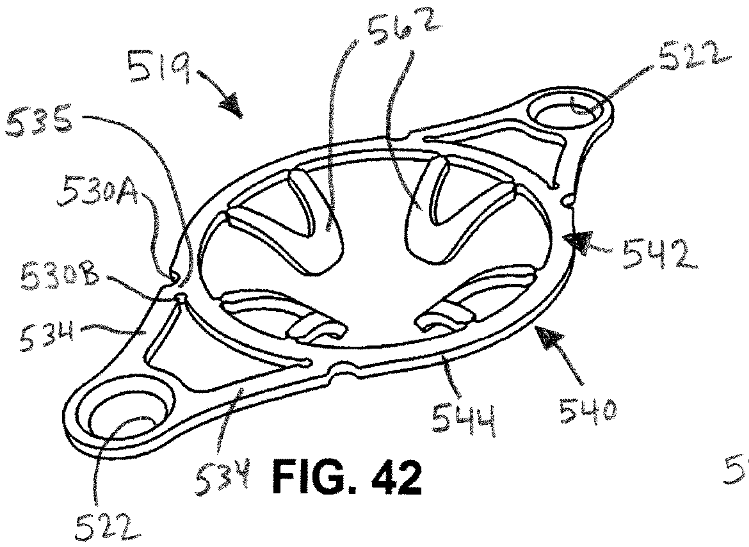
FIG. 42 is a perspective view of the support structure of the implant of FIG. 37.
Figure 43:
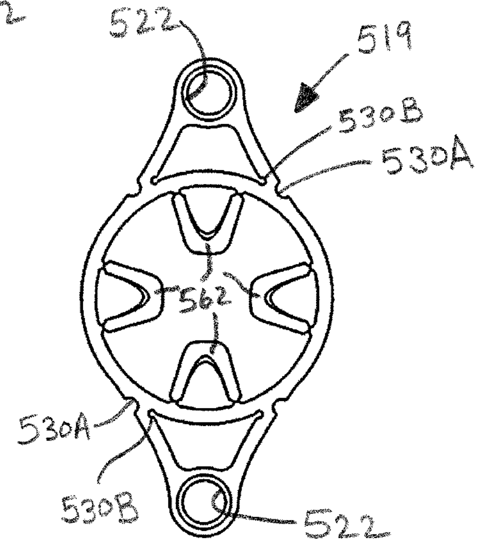
FIGS. 43-45 depict a top plan view, side plan view, and bottom plan view, respectively, of the support structure of FIG. 42.
Figure 44:
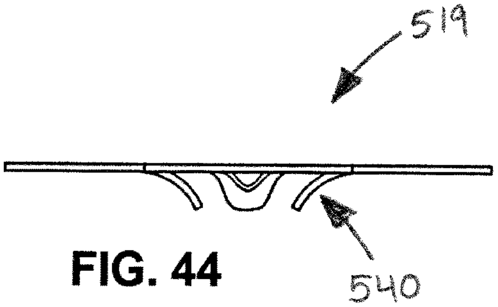
Figure 46:
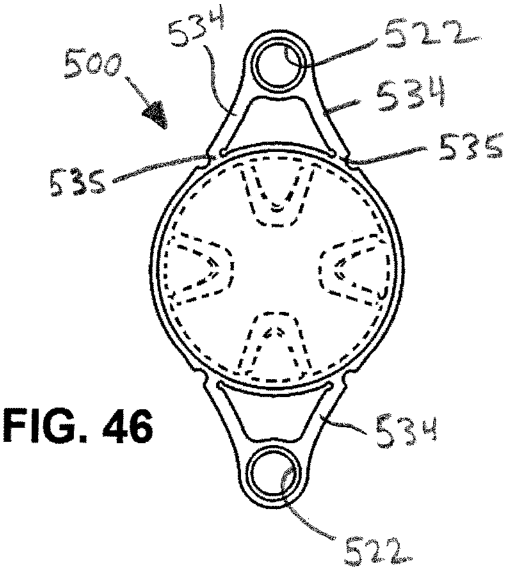
FIG. 46 is the same view as FIG. 38, wherein the portions of the support frame located within the plate are shown in broken line.
Figure 45:
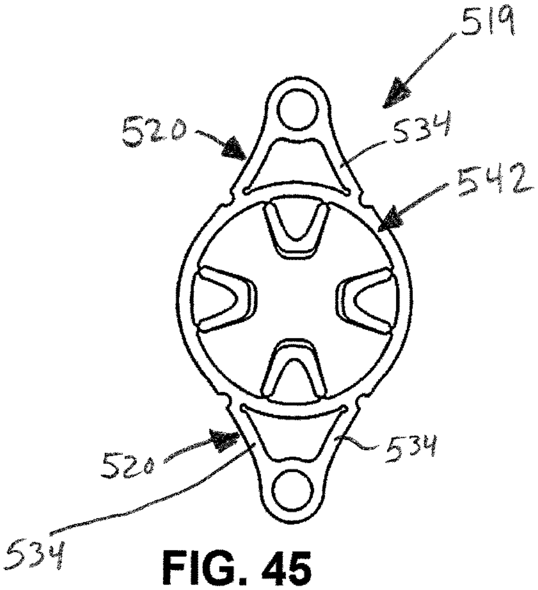

Because the outer support frame is connected to the internal support frame external to the plate (512) (i.e., at outer surface (544) of the annular ring (542)), the wire members (534) can be deformed (i.e., bent) without risk of cracking the plate (512). Deformation zones are one again provided in order to facilitate deformation of the outer support frame so that the retention eyelets and wire members can be oriented to better match the curvature of surrounding bone. Any of the previously described types of deformation zones can be employed, including regions of reduced cross-section (width and/or thickness) as well as pleated regions. In the depicted embodiment, as best seen in FIG. 42, a first arcuate notch (530A) extends into one side of the inner terminal end of the wire member (534) and a portion of the annular ring (542) adjacent to the wire member. A second arcuate notch (530B) extends into the opposite side of the inner terminal end of the wire member (534) and a portion of the annular ring (542) adjacent to that side of the wire member. As a result, a short strut (535) is formed between the inner terminal end of the wire member (534) and the outer surface (544) of the annular ring, with the short strut extending radially inward toward the central axis of the annular ring (542). The reduced width of the short struts (535) as compared to the width of the wire member (534) from which it extends, as well as the radially extending nature of the short struts (535) with respect to the annular ring (as compared to the nearly tangential orientation of the inner terminal end of the wire member (534)), results in the short struts (535) providing deformation zones where each of the wire members (534) meet the annular ring. Of course, any of the other types of deformation zones described herein can be employed instead of, or in addition to, the arcuate notches (530A, 530B).

The support structure (119, 219, 319, 419, 519) can be made from any of a variety of biocompatible materials suitable for implantation in a patient, including, for example, various metals, polymers, or even composite materials of two or more metals and/or polymers. Non-limiting examples include biocompatible and/or biodegradable polymers such as polycaprolactone, titanium, titanium alloys (e.g. Ti-6Al-4V), stainless steel, and shape memory alloys such as nitinol. The support structure can be formed in any of a variety of manners such as forging, casting, molding, extrusion, cutting (including laser cutting), etching, stamping, welding, additive manufacturing techniques, etc. In some embodiments, the support structure (119, 219, 319, 419, 519) is formed from a metal sheet that is stamped or cut (e.g., using an automated, programmable laser cutting device) in a predetermined pattern to produce a unitary support structure of constant thickness. Such a support structure (e.g., 419 or 519) will have a constant thickness throughout. In one embodiment, the support structure (419, 519) has a thickness of about 0.2 to about 0.6 mm, or about 0.3 to about 0.45 mm. Suitable metals for such fabrication techniques include titanium or titanium alloy (e.g., grade 1, 2, 3, 4, 5 or 23 titanium). Alternatively, the support structures (119, 219, 319, 419, 519) can be cut, etched, stamped, molded or otherwise formed from a biodegradable polymer such as polycaprolactone.

As yet another alternative, the support structure (119, 219, 319, 419, 519), as well as a mold negative for use in fabricating a mold for molding the biocompatible plate (112, 212, 312, 412, 512), can be manufactured using additive manufacturing techniques (sometimes referred to as 3D-printing). Any of a variety of additive manufacturing methods can be employed, including stereolithography, fused deposition modeling (also known as fused filament fabrication), selective laser sintering (including direct metal laser sintering), selective laser melting ("SLM"), electron beam melting, and other techniques known to those skilled in the art or hereafter developed. Selective laser melting is particularly useful in fabricating the support structure (119, 219, 319) from titanium, titanium alloy or other metal. Selective laser sintering is useful for fabricating the mold negative in polyamide, while fused deposition modeling, on the other hand, is particularly useful for fabricating the mold negative from, for example, PLA or ABS.

Also, any of the support structures described herein can be formed as a single, unitary structure, or made from two or more components (e.g., the inner and outer support frames) that are then attached to one another such as by welding.

While the biocompatible plate can be provided on the support structure in a variety of manners, molding the plate onto or around the inner support frame is particularly suitable. Once the support structure (119, 219, 319, 419, 519) has been fabricated, the support structure is positioned in a suitably shaped mold for the biocompatible plate (112, 212, 312, 412, 512). The plate is then molded onto the inner support frame (140, 240, 340, 440, 540). In addition to virtually eliminating the risk of fracturing the plate when portions of the outer support frame are bent for fit as well as resisting hoop stress in the plate, the exposed outer surface (144, 244, 344, 444, 544) of the inner support frame also simplifies the molding process. In particular, because the struts connecting the inner and outer support frames do not extend into the biocompatible plate (112, 212, 312, 412, 512) there is generally no need to cover the struts (or any other portion of the support structure) with silicone guards or other coverings to prevent the plate material from covering the struts during molding. Because the outer surface (144, 244, 344, 444, 544) is in the form of an exposed surface of revolution, the plate mold is configured to snugly receive the portions of the inner support frame (140, 240, 340, 440, 540) that are to remain exposed (i.e., not covered by the plate material), with no gap between, for example, the outer surface (144, 244, 344, 444, 544) of the inner support frame and the outer wall of the mold, thereby preventing any plate material from covering the outer surface during molding.

Not only does the exposed outer surface (144, 244, 344, 444, 544) of the inner support frame facilitate molding of the plate without defects in the exterior surface of the plate, it also protects the upper edge of the plate (e.g., prevents cracking at the upper edge). In the case of the implants (100, 200, 300), the exposed outer surface (144, 244, 344) also provides a smooth cylindrical surface that can be partially fit into the bore hole during implantation.

The biocompatible plates (112, 212, 312, 412, 512) can be provided in any of a variety of sizes depending on the size of the bore hole to be filled. In particular, the maximum outer diameter of the portion of the plate to be inserted into a bore hole should generally be slightly less than the diameter of the bore hole (e.g., between about 0.3 and about 1.5 mm smaller) in order to allow the plate to be easily inserted into the bore hole and to prevent fracturing of the plate during insertion.

For example, the outer diameter of the upper end of the plate (i.e., the diameter of the upper surface (113, 213, 313, 413 513) and/or the outer diameter of the plate where it meets the bottom surface (145, 245, 345, 445, 545) of the inner support frame) can be between about 0.7 and about 1.7 cm, while the diameter of the lower end of the plate is between about 0.5 and about 1.4 cm. In specific embodiments of the implants (400, 500), the outer diameter of the upper end of the plate is between about 1.25 and about 1.35 cm (to fit a 14 mm bore hole), while in other specific embodiments of implant (400, 500) the outer diameter of the upper end of the plate is between about 0.95 and about 1.05 cm (to fit an 11 mm bore hole). In specific embodiments of implants (100, 200, 300) wherein a portion of the exposed outer surface (144, 244, 344) of the inner support frame is inserted into the bore hole, the outer diameter of the outer surface (144, 244, 344) of the inner support frame can be similarly dimensioned (between about 1.25 and about 1.35 cm, or between about 0.95 and about 1.05 cm). These dimensions allow the implants to be inserted into bore holes of typical diameters (11 mm or 14 mm). In some embodiments, the plate (112, 212, 312, 412, 512) has a thickness (as measured at the center of the plate) of between about 0.2 and about 0.5 cm, or between about 0.25 and about 0.35 cm.

The upper surface (113, 213, 313, 413, 513) of the plate can be flat (e.g., 113, 213, 313), or have a slight convex curvature (e.g., 413, 513) so as to approximate the curvature of a portion of a typical skull. In some embodiments having a convexly curved upper surface, this curvature results in the plate (112, 212, 312, 412, 512) being about 0.02 to about 0.07 cm thicker at its center as compared to its thickness at its outer edge. Thus, the upper surface of the plate, even when convexly curved, is generally level with the upper surface of the retention eyelets (prior to any deformation of the outer support frame), with the upper surface of the plate extending no more than about 0.1 cm above, or no more than about 0.05 cm above, the height of the upper surface of the retention eyelets (when viewed from the side, e.g., FIG. 29A). The bottom surface (114, 214, 314, 414, 514) of the plate is flat in the depicted embodiments, but can be curved slightly, if desired.

As mentioned previously, the biocompatible plate of the various bore hole implants described herein can be composed of any of a variety of resorbable and/or stable (i.e., non-resorbable) biocompatible materials, including various types and/or combinations of polymers, ceramics and metals. In some embodiments, the plates are composed of an osteoconductive and/or osteoinductive material. Osteoconductive materials serve as a scaffold on which bone cells will attach, migrate, and grow and divide so as to form new bone on the surfaces of the plate. Osteoinductive materials induce new bone formation around the plate. An osteoconductive and/or osteoinductive plate material will facilitate bone growth in the gap between the plate and the surrounding bone. Furthermore, such materials may prevent the resorption of surrounding bone, particularly the bone flap that is not in connection with the surrounding bone, by closing the gap between the bone flap and the surrounding skull.

In some embodiments, the biocompatible plate is composed of a moldable bioceramic or biopolymer material. While bioceramic materials can be produced by sintering ceramic powders, it can be difficult to produce complex shapes in this manner. Alternatively, bioceramics can be formed by a chemical bonding route whereby the ceramic material is formed by chemical reaction, such as a cement setting and hardening reaction. In particular, a bioceramic material comprising a hydraulic cement composition can be used to mold the biocompatible plate. Non-limiting examples include cement precursor compositions comprising one or more Ca-salts such as calcium sulfates, calcium phosphates, calcium silicates, calcium carbonates and combinations thereof. As further described herein, the biocompatible plate is formed by molding the cement composition around portions of the support frame. For example, a powdered cement precursor composition is combined with either a non-aqueous water-miscible liquid or a mixture of water and a non-aqueous water-miscible liquid. The mixture is then poured or injected into a mold having the support frame positioned therein, and allowed to harden (e.g., in a water-containing bath) so as to form the plate about the support frame.

Various cement compositions that may be used to mold the plates are described, for example, in PCT Pub. No. WO 2014/091469 A1, published Jun. 19, 2014, titled "Cement-Forming Compositions, Monetite Cements, Implants and Methods for Correcting Bone Defects." Alternative cement compositions for use in molding the plates, including storage stable premixed hydraulic cement compositions, are described in PCT Pub. No. WO 2013/035083 A2, published Mar. 14, 2013, titled "Storage Stable Premixed Hydraulic Cement Compositions, Cements, Methods, and Articles." Still further cement compositions that may be used to mold the plates are described, for example, in PCT Pub. No. WO 2011/112145 A1, entitled Implants and Methods for Correcting Tissue Defects, published Sep. 15, 2011, as well as the '175 App., and PCT Pub. No. WO 2010/055483 A2, published May 20, 2010, titled "Hydraulic Cements, Methods and Products." Additional suitable cement compositions for molding the plate of the implants described herein are described in PCT Pub. No. WO 2017/051356, published Mar. 30, 2017, titled "Cement-Forming Compositions, Apatite Cements, Implants and Methods for Correcting Bone Defects." Each of the foregoing patent applications and publications is incorporated by reference herein.

In one embodiment, the compositions are calcium phosphate cement-forming compositions that comprise a monetite-forming calcium-based precursor powder and a non-aqueous water-miscible liquid. In one specific embodiment, the monetite-forming calcium-based precursor powder comprises monocalcium phosphate (monocalcium phosphate monohydrate (MCPM) and/or anhydrous monocalcium phosphate (MCPA)) and β-tricalcium phosphate in a weight ratio of 40:60 to 60:40, and from 2 to 30 weight percent, based on the weight of the precursor powder, of dicalcium pyrophosphate powder (also referred to herein as calcium pyrophosphate). The powder to liquid (wt/vol) ratio in the composition is from 2 to 6 g/ml.

In another embodiment, the compositions are calcium phosphate cement-forming compositions that comprise a monetite-forming calcium-based precursor powder and are adapted to be mixed with an aqueous liquid or exposed to an aqueous liquid to achieve hardening. In one specific embodiment, the monetite-forming calcium-based precursor powder comprises monocalcium phosphate (monocalcium phosphate monohydrate (MCPM) and/or anhydrous monocalcium phosphate (MCPA)) and β-tricalcium phosphate in a weight ratio of 40:60 to 60:40, and from 2 to 30 weight percent, based on the weight of the precursor powder, of dicalcium pyrophosphate powder (also referred to herein as calcium pyrophosphate).

The porosity of the molded plate can also be controlled, as the porosity affects bone ingrowth and the resorption time in vivo. For example, porosity may be controlled by controlling monocalcium phosphate particle size in the precursor composition, and/or adding one or more porogens to the precursor composition. In some embodiments, the molded plate has a porosity of from 40 to 50%, and in other embodiments, the porosity is about 46%.

In one specific embodiment, the monetite-forming calcium-based precursor powder mixture is mixed with a non-aqueous water-miscible liquid such as glycerol, optionally including up to 20% water (based on the total liquid volume). After mixing, the precursor mixture is injected into a mold having the support frame positioned therein. The filled mold is then exposed to water, such as by placing the mold in a water bath, and the cement is allowed to harden (e.g., 24 hours in a room temperature water bath). The implant is then removed from the mold. Further processing such as soaking the implant in water to remove glycerol residues may be performed, as necessary.

The thus-formed plate of the implant in the example described above will comprise monetite ($CaHPO_4$) and 2-30 wt. % dicalcium pyrophosphate, along with varying amounts of other materials such as β-tricalcium phosphate and minor amounts of brushite ($CaHPO_4 \cdot 2H_2O$) (e.g., less than 2 wt. % or less than 1 wt. %) (although brushite will be converted to monetite upon sterilization of the implant in an autoclave prior to implantation). The plate in some embodiments comprises at least 65 wt %, at least 70%, at least 75%, at least 80%, at least 85%, or at least 90% monetite. The presence of dicalcium pyrophosphate not only delays undesirably fast resorption of the plate but also provides osteoinductivity (i.e., promotes new bone growth around and between the plate as compared to similar monetite formulations which do not include dicalcium pyrophosphate).

In yet another embodiment, the plates are formed of a hardened monetite cement comprising at least 70 wt. % of monetite and from 3 to 30 wt. % of dicalcium pyrophosphate, or, more specifically, comprising at least 80 wt. % of monetite and from 3 to 20 wt. % of dicalcium pyrophosphate. The hardened monetite cement may further comprise β-tricalcium phosphate (β-TCP). In specific embodiments, the hardened monetite cement may comprise at least 75 wt. % of monetite, from 3 to 20 wt. % of dicalcium pyrophosphate, and from 1 to 15 wt. % of β-TCP, or at least 80 wt. % of monetite, from 3 to 15 wt. % of dicalcium pyrophosphate, and from 3 to 12 wt. % of β-TCP. In more specific embodiments, the dicalcium pyrophosphate is β-dicalcium pyrophosphate. In yet additional embodiments, the hardened monetite cement is formed from a monetite-forming precursor powder comprising monocalcium phosphate, β-TCP, and from 3 to 30 wt. %, or from 3 to 20 wt. %, based on the weight of the precursor powder, of dicalcium pyrophosphate. In specific embodiments, the weight ratio of monocalcium phosphate and β-TCP in the precursor powder is in a range of 40:60 to 60:40, or, more specifically, in a range of 45:55 to 52:48. In additional specific embodiments, the monocalcium phosphate is monocalcium phosphate monohydrate.

In still further embodiments, the plates are formed of a hardened apatite cement comprising from 1 to 30 wt. % of dicalcium pyrophosphate. In more specific embodiments, the hardened apatite cement comprises greater than 80 wt. % apatite. The hardened apatite cement may further comprise β-tricalcium phosphate (β-TCP). In specific embodiments, the hardened apatite cement may comprise greater than 80 wt. % apatite, 1 to 15 wt. % β-tricalcium phosphate, and 1 to 15 wt. % β-dicalcium pyrophosphate. In more specific embodiments, the dicalcium pyrophosphate is β-dicalcium pyrophosphate. In yet additional embodiments, the hardened apatite cement is formed from a calcium phosphate cement-forming composition comprising an apatite-forming calcium-based precursor powder comprising α-tricalcium phosphate and/or tetracalcium phosphate, and from 1 to 30 wt. %, based on the weight of the precursor powder, of dicalcium pyrophosphate powder.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. For example, the inner support frame of any one of the above-described embodiments can be used in combination with any one of the outer support frames of the above-described embodiments. Similarly, the support member arrangements of the inner support frame of any one of the above-described embodiments can be used in combination with any one of the inner support frames and any one of the outer support frames described herein (e.g., the support members (462) can be used in place of the support members (162)). Likewise, the plate arrangements of the various embodiments are interchangeable (e.g., using plate (412) in place of plate (112)). Furthermore, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art.

What is claimed is:

1. An implant for at least partially filling a bore hole in a bone comprising:

(a) a biocompatible plate having an upper surface, a bottom surface, and a central axis;

(b) a support structure comprising:

(i) an inner support frame including a ring-shaped member encircling the plate, said ring-shaped member having an exposed outer surface defining the outer diameter of the ring-shaped member and an inner surface defining the inner diameter of the ring-shaped member, and at least one support member connected to and extending inwardly from the inner surface of the ring-shaped member within said plate, and (ii) an outer support frame comprising a plurality of fastening points adapted for attaching the implant to bone surrounding a bore hole in which the plate is inserted, said outer support frame connected to and extending away from the outer surface of the ring-shaped member;

wherein at least a portion of said at least one support member extends inwardly from the inner surface of the ring-shaped member at an angle with respect to a plane that is orthogonal to the central axis of the plate such that the depth of the support member within the plate varies along its length, and wherein each of said support members is in the form of a wire loop having first and second connected legs, the first leg extending inwardly and downwardly away from a first portion of the inner surface of the ring-shaped member, and the second leg extending inwardly and downwardly away from a second portion of the inner surface of the ring-shaped member.

2. The implant of claim 1, wherein said inner support frame comprises a plurality of said support members spaced about and extending inwardly from the inner surface of the ring-shaped member such that the depth of each support member within the plate varies along its length.

3. The implant of claim 2, wherein each of said support members extends radially inward from the inner surface of the ring-shaped member a distance that is less than one half the maximum diameter of the plate.

4. The implant of claim 1, wherein said implant is configured to at least partially fill a bore hole in a patient's skull, and said outer support frame is deformable such that at least a portion of the outer support frame can be deformed to match the curvature of a patient's skull.

5. The implant of claim 1, wherein said biocompatible plate comprises a hydraulic cement composition.

6. The implant of claim 1, wherein said fastening points comprise retention eyelets spaced away from said outer surface of said inner support frame.

7. The implant of claim 6, wherein said outer support frame encircles the outer surface of said inner support frame.

8. The implant of claim 6, wherein the outer support frame includes a plurality of wire members, each extending between either: (i) a pair of said retention eyelets; or (ii) a retention eyelet and the outer surface of said inner support frame.

9. The implant of claim 8, wherein the outer frame includes six of said retention eyelets arranged about the outer periphery of the outer surface of the inner support frame, and six of said wire members, each wire member extending between a pair of adjacent retention eyelets and connected to the outer surface of said inner support frame such that the wire members and eyelets encircle the outer surface of said inner support frame.

10. The implant of claim 6, wherein the outer support frame includes a plurality of wire members, wherein each retention eyelet is spaced away from the outer surface of the inner support frame by at least two of said wire members connected to the retention eyelet and the outer surface of the inner support frame.

11. The implant of claim 6, wherein the outer frame includes only two of said retention eyelets located at opposite ends of the outer support frame and a plurality of wire members, wherein each wire member extends between either: (i) a pair of said retention eyelets; or (ii) a retention eyelet and the outer surface of said inner support frame.

12. The implant of claim 6, wherein said outer support frame includes one or more deformation zones for facilitating deformation of outer support frame.

13. The implant of claim 1, wherein the outer support frame further comprises a plurality of struts connecting the outer support frame to the outer surface of the inner support frame.

14. The implant of claim 1, wherein the outer support frame further comprises a plurality of struts, wherein said wire members connected to a retention eyelet and the outer surface of the inner support frame are connected to the outer surface of the inner support frame by one of said struts.

15. The implant of claim 1, wherein:

said biocompatible plate has an upper surface, a bottom surface, a central axis, and an outer surface of revolution around said central axis, said ring-shaped inner support frame comprises a flat, annular ring, and said flat annular ring is positioned orthogonal to the central axis of the plate.

16. The implant of claim 1, wherein the ring-shaped inner support frame has an annular upper surface extending between said inner and outer surfaces, and further wherein said plate extends over only a portion of said annular upper surface.

* * * * *